US006784283B2

(12) United States Patent
Andersen et al.

(10) Patent No.: US 6,784,283 B2
(45) Date of Patent: Aug. 31, 2004

(54) PEPTIDE ANTIBIOTICS

(75) Inventors: Raymond J. Andersen, Vancouver (CA); Michael T. Kelly, Surrey (CA); Todd A. Barsby, Vancouver (CA)

(73) Assignees: The University of British Columbia, Vancouver (GB); Ocean Pharmaceuticals, Inc., Vancouver (GB)

( * ) Notice: Subject to any disclaimer, the term of this patent is extended or adjusted under 35 U.S.C. 154(b) by 214 days.

(21) Appl. No.: 09/794,229

(22) Filed: Feb. 26, 2001

(65) Prior Publication Data

US 2002/0035239 A1 Mar. 21, 2002

Related U.S. Application Data

(60) Provisional application No. 60/185,097, filed on Feb. 25, 2000.
(51) Int. Cl.[7] .................................................. C07K 7/00
(52) U.S. Cl. ........................ 530/327; 530/324; 530/325; 530/326; 514/12; 514/13; 514/14
(58) Field of Search ................................ 530/324–330; 514/12–17

(56) References Cited

FOREIGN PATENT DOCUMENTS

WO      WO 98/04584    *  2/1998

OTHER PUBLICATIONS

Barsby T. et al. (2001) Organic Letters 3(3):437–440.*
Bauer SM. & Armstrong RW. (1999) J. Am. Chem. Soc. (1999) 121(27):6355–6366.*
Degrado WF. & Kaiser ET. (1980) J. Org. Chem. 45(7):1295–1300.*
Edmond MB. et al. (1995) Clinical Infectious Diseases 20(5):1126–1133.*
Fournier A. et al. (1988) Int. J. Peptide Protein Res. 31:86–97.*
Fuji N. et al. (1987) J. Chem. Soc. Chem. Comm. 274–275.*
Gerard J. et al. (1996) Tetrahedron Letters 37:7201–7204.*
Kaiser ET. et al. (1970) Anal. Biochem. 34(2):595–598.*
Katz E. & Demain AL. (1977) Bacteriol. Rev. 41(2):449–474.*
Kosui N. et al. (1981) Int. J. Peptide Protein Res. 18(2):127–134.
Merrifield RB. (1963) J. Am. Chem. Soc. 85(14):2149–2154.
Ohno M. & Izumiya N. (1966) J. Am. Chem. Soc. 88(2):376–378.
Okamato K. et al. (1977) Bull. Chem. Soc. Jpn. 50:231–236.
Osapay G. et al. (1990) Tetrahedron Letters 31(43):6121–6124.
Valentekovich RJ. & Schreiber SL. (1995) J. Am. Chem. Soc. 117(35):9069–9070.

* cited by examiner

*Primary Examiner*—Christopher S. F. Low
*Assistant Examiner*—David Lukton
(74) *Attorney, Agent, or Firm*—Bret E. Field; Bozicevic, Field & Francis

(57) ABSTRACT

N- and C-modified linear cationic peptides having antibiotic activity are disclosed, which peptides are particularly active against gram positive bacteria.

25 Claims, No Drawings

PEPTIDE ANTIBIOTICS this application claims the benefit of provisional Application No. 60/185,097 filed Feb. 25, 2000.

TECHNICAL FIELD

The present invention relates to cationic peptides having antibiotic activity.

BACKGROUND OF THE INVENTION

Methicillin-resistant strains of *Staphylococcus aureus* (MRSA) cause infections that are refractory to standard anti-staphylococci antibiotics, and in many cases vancomycin is the antibiotic of last resort. Consequently, it is of great concern that vancomycin-resistant strains of MRSA may develop.

Infections due to enterococci have been difficult to treat for many years because these organisms are intrinsically resistant to many antibiotics. Ampicillin has been the mainstay for treatment of uncomplicated enterococcal infections, but many strains have now become resistant to ampicillin. vancomycin is again the only effective treatment for these ampicillin-resistant enterococcal infections. In the past few years, vancomycin-resistant enterococcal strains(VRE) have begun to appear and they are rapidly spreading across North America. There are no effective antibiotics currently available for such organisms and the recent report of an outbreak of VRE with a 73% mortality rate has highlighted the seriousness of the situation, See Edmond, M. B. et al., Clinical Infections Diseases 20: 1126-33, 1995.

New compounds are needed for the treatment of antibiotic-resistant pathogens, particularly gram positive strains of human pathogens. The present invention is directed to fulfilling this need, and provides related advantages as described herein.

SUMMARY OF THE INVENTION

This invention provides an antibiotic peptide of formula (1):

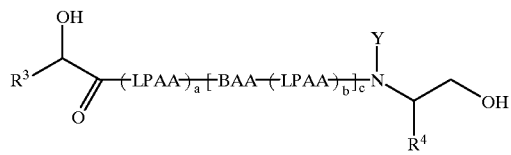

wherein:

a, b, and c are independently selected integers, wherein a=1–10, b=1–10, and c=2–5;

Y is selected from the group consisting of: H; OH; and, a linear, branched or cyclic, saturated or unsaturated alkyl of one to ten carbon atoms;

LPAA is an amino acid residue having the structure —NX—$C^\alpha R^1$—CO—, wherein for each LPAA in the peptide, $R^1$ is independently selected from the group consisting of: hydrogen; a linear, branched or cyclic, saturated or unsaturated alkyl containing one to ten carbons atoms optionally substituted with —OH, —OR, —SH, —SR, —SOCR, —NHCOR, —I, —Br, —Cl, —F —CN, —$O_2CR$, —$CO_2R$, —CHO, —COR, —$CONH_2$, —CONHR, —$CONR_2$, —COSR, —SOR, or —$SO_2R$; benzyl, in which a phenyl ring of the benzyl is optionally substituted with R, —OH, —OR, —SH, —SR, —SOCR, —NHCOR, —I, —Br, —Cl, —F, —CN, —$CO_2R$, —CHO, —COR, —$CONH_2$, —CONHR, —$CONR_2$, —COSR —$NO_2$, —SOR, or —$SO_2R$; and, arylalkyl in which an alkyl group of the arylalkyl has two to ten carbon atoms and is linear, branched or cyclic, saturated or unsaturated, optionally substituted with —OH, —OR, —$O_2CR$, —SH, —SR, —SOCR, —NHCOR, —I, —Br, —Cl, —F, —CN, —$CO_2R$, —CHO, —COR, —$CONH_2$, —CONHR, —$CONR_2$, —COSR —$NO_2$, —SOR, or —$SO_2R$, and in which an aryl ring of the arylalkyl is phenyl, or indole, optionally substituted with R, —OH, —OR, —$O_2CR$, —SH, —SR, —SOCR, —NHCOR, —I, —Br, —Cl —CN, —$CO_2R$, —CHO, —COR, —$CONH_2$, —CONHR, —$CONR_2$, —COSR —$NO_2$, —SOR, or —$SO_2R$; wherein for $R^1$. R is a linear, branched or cyclic, saturated or unsaturated alkyl of one to ten carbon atoms, and providing that when $R^1$ is joined to $C^\alpha$ by a single bond, H is also present joined to $C^\alpha$; and, for each LPAA in the peptide, X is independently selected from the group consisting of: H; OH; and, a linear, branched or cyclic, saturated or unsaturated alkyl group containing one to ten carbons;

BAA is an amino acid residue having the structure —NX—$CHR^2$—CO—, wherein for each BAA in the peptide, $R^2$ is independently selected from the group consisting of: a linear, branched or cyclic, saturated or unsaturated alkyl group of one to ten carbons, substituted with one of $NH_2$, NRH, $NR^2$, $NR_3^+$, guanidinyl (—NH—CNH—$NH_2$), and imidazole, and optionally substituted with —OH, —OR, —SH, —SR, —SOCR, —NHCOR, —I, —Br, —Cl, —F, —CN, —$CO_2R$, —CHO, —$O_2CR$, —COR, —$CONH_2$, —CONHR, —$CONR_2$, —COSR, —SOR, or —$SO_2R$; benzyl in which a phenyl ring of the benzyl is substituted with one of $NH_2$, NRH, $NR_2$, $NR_3^+$, and optionally substituted with R, —OH, —OR, —$O_2CR$, —SH, —SR, —SOCR, NHCOR, —I, —Br, —Cl, —F, —CN, —$CO_2R$, —CHO, —COR, —$CONH_2$, —CONHR, —$CONR_2$, —COSR —$NO_2$, —SOR, or —$SO_2R$; arylalkyl in which an alkyl of the arylalkyl is linear, branched or cyclic, saturated or unsaturated of two to ten carbons, optionally substituted with —OH, —OR, —$O_2CR$, —SH, —SR, —SOCR, —NHCOR, —I, —Br, —Cl, —F, —CN, —$CO_2R$, —CHO, —COR, —$CONH_2$—CONHR, —$CON_2$, —COSR, —$NO_2$, —SOR, or —$SO_2R$, and in which an aryl ring of the arylalkyl is phenyl substituted with one of $NH_2$, NRH, $NR_2$, $NR^+$, indole substituted with one of $NH_2$, NRH, $NR_2$, $NR_3^+$, pyridine, or imidazole; and wherein the aryl ring is optionally substituted with R, —OH, —OR, —$O_2CR$, —SH, —SR, —SOCR, —NHCOR, —I, —Br, —Cl, —F, —CN, —$CO_2R$, —CHO, —COR, —$CONH_2$, —CONHR, —$CONR_2$, —COSR —$NO_2$, —SOR, or —$SO_2R$; wherein for $R^2$, R is a linear, branched or cyclic, saturated or unsaturated alkyl of one to ten carbon atoms; and, for each BAA in the peptide X is independently selected from the group consisting of: H; OH; and a linear, branched or cyclic, saturated or unsaturated alkyl of one to ten carbons; and, $R^3$ and $R^4=R^1$, and $R^3$ and $R^4$ are the same or different.

The term LPAA denotes an amino acid residue having a lipophilic character as compared to BAA. For example, LPAA includes the amino acids glycine, alanine, valine, butyrine, leucine, isoleucine, asparagine, glutamine, tryptophan, tyrosine, phenylalanine, methionine, methionine sulfoxide, threonine, serine, cysteine, and the α,β-unsaturated analogs of these amino acids except glycine. The term BAA denotes an amino acid residue having a basic character as compared to LPAA. For example, BAA includes the amino acids ornithine, lysine, histidine, and arginine.

The peptide of formula (1) has an N-terminus modified by the presence of an alpha hydroxy acyl group, and a C-terminus reduced to a primary alcohol. $R^3$ at the N-terminus may be an alkyl group such as —CH(CH$_3$) CH$_2$CH$_3$ as is the case for Bogorol A-D as disclosed herein. At the C-terminus, Y in formula (1) may be hydrogen and $R^4$ may be —CH(CH$_3$)$_2$, as is the case for Bogorol A-D described herein.

The values of each a, b, and c integer in formula (1) are independently selected The structure of each BAA or LPAA in the peptide may be the same or different as compared to any other BAA or LPAA in the peptide. The number of LPAA components may differ as between different regions along the linear structure of the peptide. Thus, each-[-BAA-(-LPAA)$_b$-]-unit of the peptide may have a different BAA residue, different value for b, and different LPAA residues, as compared to any other such unit.

A peptide of formula (1) preferably will have from 10–25 LPAA and BAA residues combined, more preferably from 10–20 and even more preferably from 12–18, which numbers do not include the C-terminal modified amino acid residue Preferably, the number of BAA residues (denoted by the integer c), will be 2–3. Bogorol A-D have a total of 12 LPAA and BAA residues combined, which when added to the modified C-terminal residue, results in a total of 13 amino acid and modified amino acid residues, including 3 BAA residues. Preferably the integer b will be 2–6, more preferably 2–4, and most preferably 2–3. Each BAA residue is preferably separated by from 2–4 and more preferably 2–3 LPAA residues, which means that the integer b is 2–4 or 2–3, but not necessarily at the C-terminus of the peptide. Preferably, the number of LPAA residues at each of the N and C termini of the peptide will be 1–5, more preferably 1–3 and most preferably, 2.

Peptides of this invention may be ordered such that a basic side group of each BAA is aligned along an axis parallel to a central axis of the peptide when the peptide is in an α-helix configuration. This ordering may be achieved by spacing each BAA residue according to the number of residues in each turn of such a helix and providing a particular stereochemical configuration for each BAA residue. For example, the stereochemical configuration of the ornithine and lysine residues of Bogorol A-D (from the N to the C terminus) may be D, D, L or D, L, D, with each of these basic amino acid residues being separated by 2–3 (preferably 3) LPAA residues.

Preferred peptides of this invention have one or more of the following limitations:

1) LPAA is an amino acid selected from the group consisting of: glycine; alanine; valine; butyrine; leucine; isoleucine; asparagine; glutamine; tryptophan, tyrosine; phenylalanine; methionine; methionine sulfoxide; threonine; serine; cysteine; and α,β-unsaturated analogs of each of said amino acids except glycine; BAA is selected from the group consisting of: ornithine; lysine; histidine; and arginine; and, $R^3$ and $R^4$ are independently selected from the group consisting of: hydrogen; methyl; ethyl; n-propyl; isopropyl; n-butyl; isobutyl; sec-butyl; benzyl; and, p-hydroxybenzyl;

2) LPAA is selected from the group consisting of: valine; leucine; isoleucine; tyrosine; phenylalanine; methionine; methionine sulfoxide; threonine; and dehydrobutyrine (DBH); BAA is selected from the group consisting of: ornithine; lysine; and arginine; and, $R^3$ and $R^4$ are independently selected from the group consisting of: hydrogen; methyl; ethyl; n-propyl; isopropyl; n-butyl; isobutyl; sec-butyl; benzyl; and p-hydroxybenzyl;

3) LPAA is selected from the group consisting of: valine; leucine; isoleucine; tyrosine; phenylalanine; methionine; methionine sulfoxide; threonine; and dehydrobutyrine (DBH); BAA is selected from the group consisting of: ornithine; lysine; and arginine; and, $R^3$ and $R^4$ are independently selected from the group consisting of: isopropyl; isobutyl; and sec-butyl;

4) a is 1–5; c is 2–5; b is 2–6; and 5) a is 2; c is 3; b is 2–3.

Preferred peptides of this invention may comprise (in a N to C terminal direction) a tyrosine-isoleucine dipeptide as the two LPAA residues immediately preceding the modified C-terminal amino acid residue. Preferred peptides may also comprise (in a N to C terminal direction) the following sequence of amino acid residues: (leucine, methionine, or valine)-ornithine-isoleucine-valine-valine-lysine-valine-leucine-lysine. Preferred peptides may also comprise DHB or threonine (preferably DHB) as the LPAA at the N-terminus of the peptide. When an LPAA comprises $R^1$ joined to the α-carbon of the residue ($C^\alpha$) by a single bond, hydrogen is also joined to $C^\alpha$, as would be the case for a common amino acid such as valine or leucine. When an LPAA comprises $R^1$ joined to $C^\alpha$ by a double bond (such as is the case for DHB), there is no hydrogen joined to $C^\alpha$.

Naturally occurring peptides of this invention are provided as isolated peptides, i.e. in a substantially purified form. A substantially purified form is one wherein one or more peptides of this invention constitute at least about 1 weight percent of a composition, preferably at least about 10 weight percent, more preferably at least about 30 weight percent, still more preferably at least about 50 weight percent, yet still more preferably at least about 70 weight percent, and yet still more preferably at least about 95 weight percent, and most preferably at least about 99 weight percent.

Peptides of this invention may be provided as salts, which salts include acid or base addition salts, depending on whether the moiety on the peptide (e.g. an amino acid side group) being connected to a salt is a basic or acidic moiety. Preferably, the salt will be acceptable for pharmaceutical purposes.

This invention also provides peptides of this invention and pharmaceutically acceptable salts thereof, in a pharmaceutical composition. A pharmaceutical composition of the invention may not necessarily contain a peptide of this invention in a substantially purified form because the composition may contain carriers, diluents, or other materials suitable for use in pharmaceutical compositions, in admixture with the peptide.

This invention also provides a method of treating bacterial infection, comprising administering to a patient having a bacterial infection, an effective amount of a peptide, peptide salt, or pharmaceutical composition of this invention. Preferably, the effective amount will be sufficient to relieve one or more symptoms associated with or due to the bacterial infection.

This invention also provides the use of a peptide, peptide salt, or a pharmaceutical composition of this invention as an antibiotic. Such antibiotic use includes use for the treatment of bacterial infections, including infections by gram-positive bacteria.

This invention also provides the use of a peptide, peptide salt, or pharmaceutical composition of this invention for the preparation of an antibiotic medicament. Such a medicament may be suitable for use against bacteria, including gram-positive bacteria.

DETAILED DESCRIPTION OF THE INVENTION

Peptides of the invention include the solvates, salts (acid- or base-addition salts, depending on whether the amino acid sidechain being converted to a salt is basic or acidic, respectively), and derivatives or analogs such as esters (derivatives of alcohol functionalities on the C and N terminal residues and/or a tyrosine phenol), amines (derivatives of amino acid sidechains containing an amino group), ethers (derivatives of amino acid and N- and C-terminal modified amino acid sidechains containing an hydroxyl group) and amides (derivatives of amino acid sidechains containing either an amine or carboxylic acid group).

Salts may contain at least one negatively charged ion selected from chloride, bromide, sulfate, phosphate, $C_{1-15}$ carboxylate, methanesulfonate and p-toluenesulfonate, which are exemplary only. Exemplary $C_{1-15}$ carboxylates include acetate, glycolate, lactate, pyruvate, malonate, succinate, glutarate, fumarate, malate, tartarate, citrate, ascorbate, maleate, hydroxymaleate, benzoate, hydroxybensoate, phenylacetate, cinnamate, salicylate and 2-phenoxybenzoate.

Salts may contain at least one positively charged ion selected from lithium, sodium, potassium, beryllium, magnesium, calcium and quaternary ammonium ions, which are exemplary positively charged ions. Exemplary quaternary ammonium ions include tetraalkylammonium, and tri-alkylaralkylammonium ions.

Derivatives or analogs may have an amine group of an ornithine or lysine sidechain being a secondary, tertiary or quaternary amine group. Other amino acid sidechains may be in a derivative form as well. Exemplary ornithine or lysine sidechains have the formula —CH$_2$—CH$_2$—CH$_2$—NHR, —CH$_2$—CH$_2$—CH$_2$—N(R)$_2$ or —CH$_2$—CH$_2$—CH$_2$—N(R)$_3$ wherein R is an alkyl group that may be of straight chain, or where possible, of cyclic or branched structure and may contain one or more alkene, alkyne, or aromatic functionalities; or an acyl group that may be of straight chain, or where possible of cyclic or branched structure and may contain one or more alkene, alkyne, or aromatic functionalities.

In other derivatives, a hydroxyl group of a tyrosine sidechain, a hydroxyl group of the α-hydroxy acyl N-terminal residue, or the primary alcohol of the C-terminal residue may be converted to an ether or ester group, and other amino acid sidechains are optionally in a derivative form as well. For example, a tyrosine sidechain may have the formula —CH$_2$—C$_6$H$_4$—O—R, wherein C$_6$H$_4$ is an aromatic ring and —O—R is in the para position, and R is a $C_{1-15}$ alkyl group so as to form an ether where the alkyl group may be of straight chain, or where possible, of cyclic or branched structure and may contain one or more alkene, alkyne, or aromatic functionalities; or a $C_{1-15}$ acyl group so as to form an ester, where the acyl group may be of straight chain, or where possible, of cyclic or branched structure and contain one or more alkene, alkyne, or aromatic functionalities.

Peptides of this invention include peptides having a "non-natural" stereochemistry at one or more of the carbons of the component amino acids as well as either epimer of the modified C- and N-terminal residues. The term "non-natural" refers to stereochemistry that differs from that of naturally occurring peptides of this invention, such as Bogorol A. In structural formula of naturally occurring peptides such as Bogorol A as set out herein, "natural" stereochemistry may be indicated by wedged and dashed lines according to the standard stereochemical convention. Use of 'wavy' lines attached to a chiral center indicates that no particular configuration is represented by the formula.

This invention is directed to various analogs of naturally occurring compounds. In the below-listed structure, no stereochemistry is designated because the analogs of the invention may have any possible stereochemistry at each atom capable of having more than one stereochemical arrangement of substituents.

Peptides of this invention may be described in terms of formula (2):

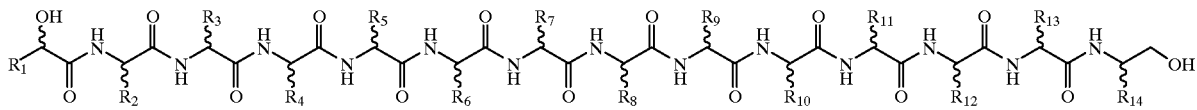

(2)

wherein:

$R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may independently be hydrogen; or a linear, branched or cyclic, saturated or unsaturated alkyl group containing one to ten carbons optionally substituted with —OH, —OR, —O$_2$CR, —SH, —SR, —SOCR, —NH$_2$, —NHR, —NHR$_2$, —NHCOR, —I, —Br, —Cl, —F, —CN, —CO$_2$H, —CO$_2$R, —CHO, —COR, —CONH$_2$, —CONHR$_2$—CONR$^2$, —COSH, —COSR —NO$_2$, —SO$_3$—, —SOR, —SO$_2$R, —NH—CN—NH$_2$ (guanidinyl); or benzyl where the phenyl ring may be substituted with R, —OH, —OR, —O$_2$CR, —SH, —SR, —SOCR, —NH$_2$, —NHR, —NHR$_2$, —NHCOR, —I, —Br, —Cl, —F, —CN, —CO$_2$H, —CO$_2$R, —CHO, —COR, —CONH$_2$, —CONHR, —CONR$_2$, —COSH, —COSR —NO$_2$, —SO$_3$—, —SOR, —SO$_2$R; or arylalkyl where the alkyl group may be linear, branched or cyclic, saturated or unsaturated containing two to ten carbons that may be substituted with —OH, —OR, —O$_2$CR —SH, —SR, —SOCR, —NH$_2$, —NHR, —NHR$_2$, —NHCOR, —I, —Br, —Cl, —F, —CN, —CO$_2$H, —CO$_2$R, —CHO, —COR, CONH$_2$, —CONHR, —CONR$_2$, —COSH, —COSR —NO$_2$, —SO$_3$—, —SOR, —SO$_2$R and where the aryl ring may be phenyl, indole, or imidazole substituted with R, —OH, —OR, —O$_2$CR, —SH, —SR, —SOCR, —NH$_2$, —NHR, —NHR$_2$, —NHCOR, —I, —Br, —Cl, —F, —CN, —CO$_2$H, —CO$_2$R, —CHO, —COR, —CONH$_2$, —CONHR, —CONR$_2$, —COSH, —COSR —NO$_2$, —SO$_3$—, —SOR, —SO$_2$R; and R is a linear, branched or cyclic, saturated or unsaturated alkyl group containing one to ten carbons. Preferred analogs may have one to four amino acid residue as present in Bogorol A replaced with a different amino acid residue.

In another aspect, peptides of this invention are linear compounds which may be described in terms of the shorthand structure shown below.

Formula A

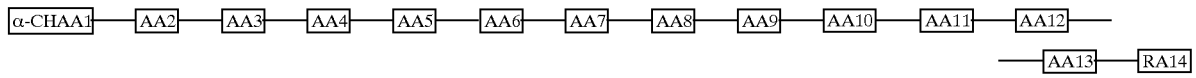

In Formula A, AA2 through AA13 are generic symbols, each representing an amino acid residue, or a salt or derivative thereof as defined herein. RA14 represents a modified carboxyl terminal amino acid where the carboxyl group has been reduced to a primary alcohol (e.g. valinol). αOHAA1 represents an alpha hydroxy acid modified residue. Each line between neighbouring (attached) residues represents an amide (also known as a peptide) bond formed between neighbouring residues, as well as the isosteres thereof. "Isostere" means a modified form of the normal peptide bond (—C(O)NH—) between attached amino acid residues, such as —CH$_2$NH— (reduced), C(O)N(SH$_3$) (N-methylamide), —COCH$_2$— (keto), —CH(OH)CH$_2$— (hydroxy), —CH(NH$_2$)CH$_2$— (amino), —CH$_2$CH$_2$— (hydrocarbon), or —NHC(O)— (inverted normal peptide bond). Preferably the compounds of the present invention are not in isosteric forms.

Except where otherwise stated, throughout this specification the recitation of a compound denotes all possible isomers within the structural formula given for those compounds, in particular optical isomers. Unless otherwise stated definitions are to be regarded as covering mixtures of isomers, and individual isomers, including racemic mixtures, where they can be resolved.

The compounds of the present invention contain multiple asymmetric carbon atoms and thus exist as enantiomers and diastereomers. Unless otherwise noted, the present invention includes all enantiomeric and diastereomeric forms of the compounds. Pure stereoisomers, mixtures of enantiomers and/or diastereomers, and mixtures of different compounds of the invention are included within the scope of the present invention. Also included are epimers of the C and N terminal modified amino acids.

Except if otherwise stated, definitions of compounds in this specification may be regarded as covering all possible esters of the compounds. In particular, except if otherwise stated, the recitation of amino acid residue having a carboxylic acid group is to be regarded as a recitation of all possible esters of that carboxylic acid.

Except if otherwise stated, definitions of compounds in this specification having phenolic groups may be regarded as covering all possible ethers or esters of the phenolic hydroxyl group.

Peptides of this invention may be described in terms of formula (3) shown below:

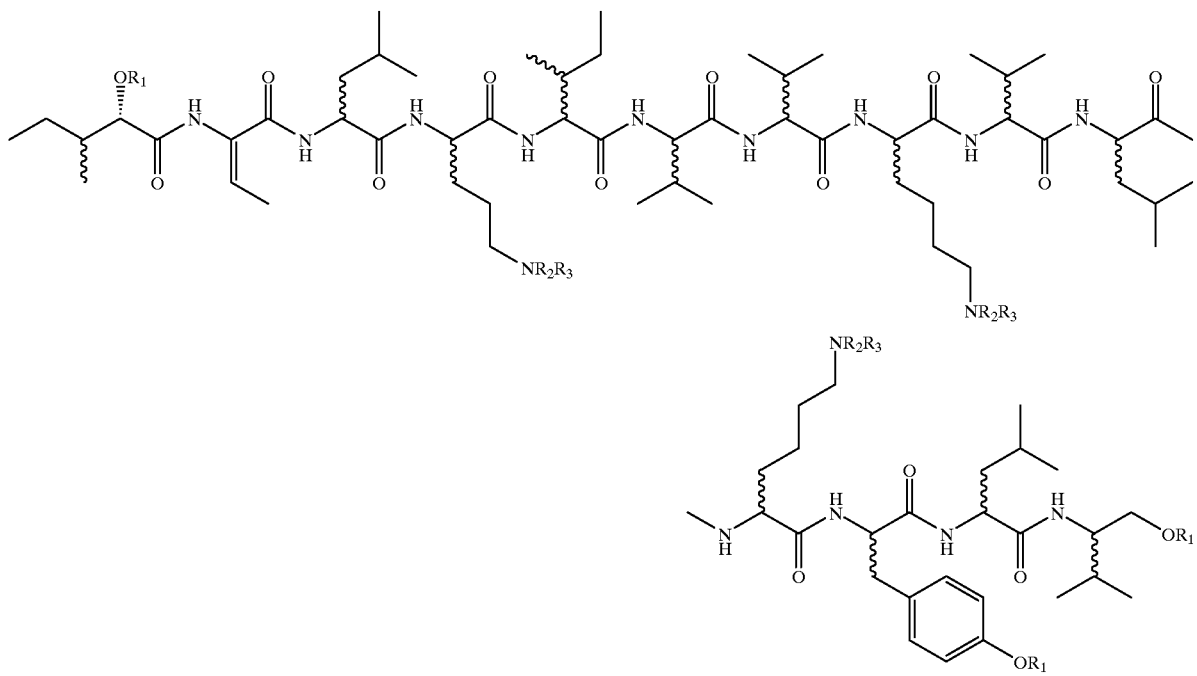

(3)

wherein:

R$^1$, R$^2$, and R$^3$ may independently represent a hydrogen atom: or an alkyl group that may be of straight chain or where possible, of cyclic or branched structure and may contain one or more alkene, alkyne, or aromatic functionalities; or an acyl group that may be of straight chain, or where possible, of cyclic or branched structure and way contain one or more alkene, alkyne, or aromatic functionalities.

Peptides of this invention may also be described in terms of Formula B.

Formula B

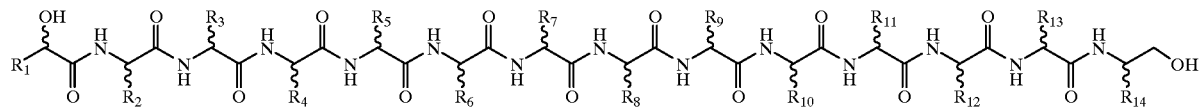

wherein:

$R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may independently be hydrogen; or a linear, branched or cyclic, saturated or unsaturated alkyl group containing one to ten carbons optionally substituted with —OH, —OR, —O$_2$CR, —SH, —SR, —SOCR, —NH$_2$, —NHR, —NHR$_2$, —NHCOR, —I, —Br, —Cl, —F, —CN, —CO$_2$H, —CO$_2$R, —CHO —COR, —CONH$_2$, —CONHR, —CONR$_2$, —COSH, —COSR, —NO$_2$, —SO$_3$—, —SOR, —SO$_2$R, —NH—CN—NH$_2$ (guanidinyl); or benzyl where the phenyl ring may be substituted with R, —OH, —OR, —O$_2$CR, —SH, —SR, —SOCR, —NH$_2$, —NHR, —NHR$_2$, —NHCOR, —I, —Br, —Cl, —F, —CN, —CO$_2$H, —CO$_2$R, —CHO, —COR, —CONH$_2$, —CONHR, —CONR$_2$, —COSH, —COSR, —NO$_2$, —SO$_3$—, —SOR, —SO$_2$R; or arylalkyl where the alkyl group may be linear, branched or cyclic, saturated or unsaturated containing two to ten carbons that may be substituted with —OH, —OR, —O$_2$CR, —SH, —SR, —SOCR, —NH$_2$, —NHR, —NHR$_2$, —NHCOR, —I, —Br, —Cl, —F, —CN, —CO$_2$H, —CO$_2$R, —CHO, —COR, —CONH$_2$, —CONHR, —CONR$_2$, —COSH, —COSR, —NO$_2$, —SO$_3$—, —SOR, —SO$_2$R and where the aryl ring may be phenyl, indole, or imidazole substituted with R, —OH, —OR, —O$_2$CR, —SH, —SR, —SOCR, —NH$_2$, —NHR, —NHR$_2$, —NHCOR, —I, —Br, —Cl, —F, —CN, —CO$_2$H, —CO$_2$R, —CHO, —COR, —CONH$_2$, —CONHR, —CONR$_2$, —COSH, —COSR, —NO$_2$, —SO$_3$—, —SOR, —SO$_2$R; and R is a linear, branched or cyclic, saturated or unsaturated alkyl group containing one to ten carbons.

Peptides of this invention include the following peptides termed Bogoral A-D:

Bogorol A

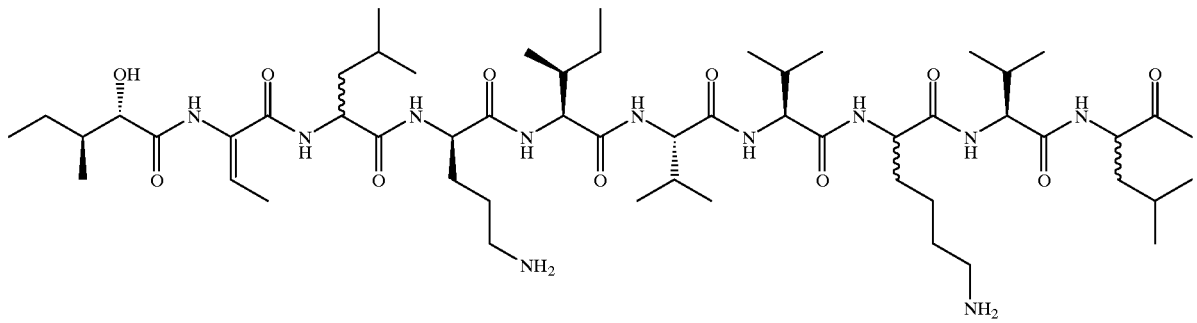

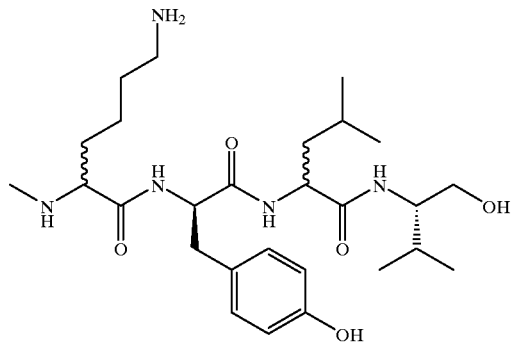

Bogorol B
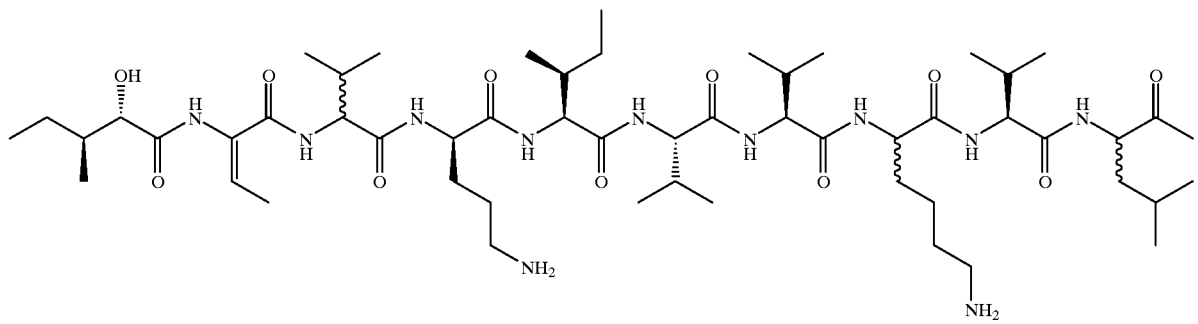
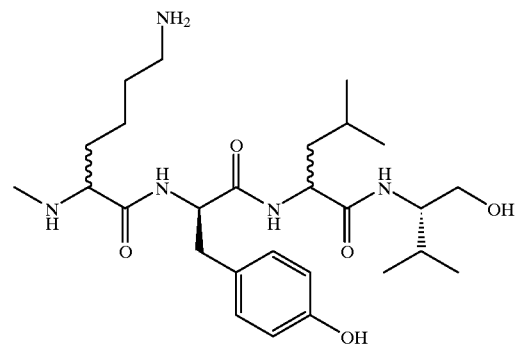
Bogorol C
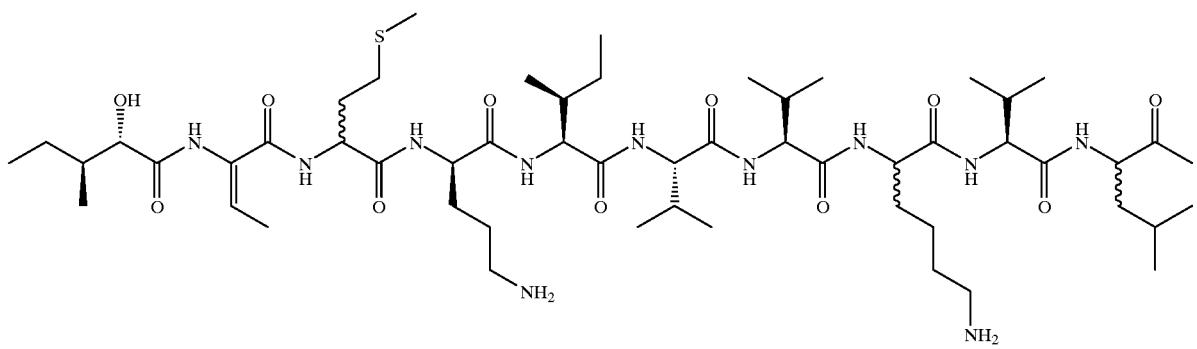
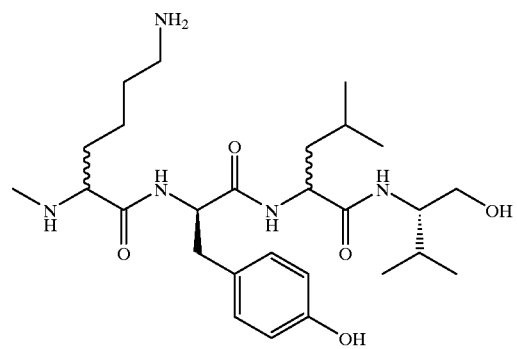

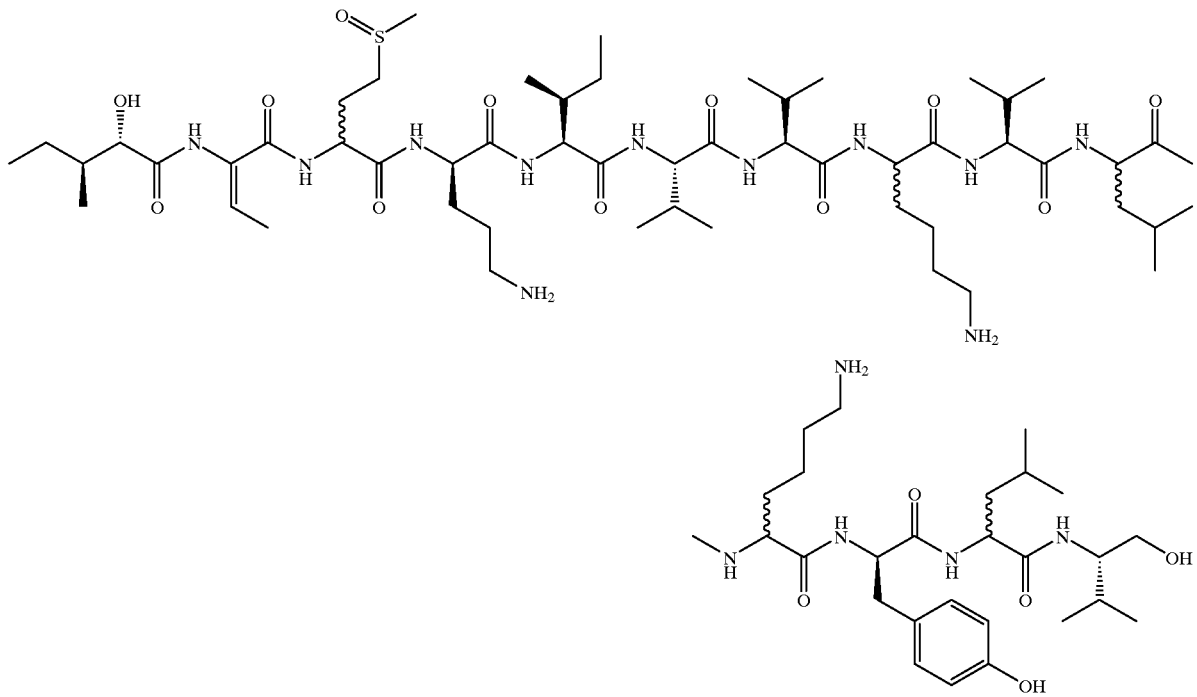

Bogorol D

The compounds of the present invention may be prepared in vitro, using solid phase or solution peptide synthesis techniques, or may be prepared in vivo, from microorganism ATCC 55797. Solution phase techniques as set forth in K. Okamato, K. et al. *Bull. Chem. Soc. Jpn.* 50:231–236 (1977), Ohno, M. et al. *J. Am. Chem. Soc.* 88(2):376–377 and Kosui, N. et al. *Int. J. Peptide Protein Res.* 18:127–134 (1981) may be modified to prepare the linear peptides of the present invention, merely by appropriate substitution of the suitably protected amino acids, reduced amino acids, or α-hydroxy acids. The compounds of the invention may also be isolated from micro-organism ATCC 55797 under appropriate conditions.

Ion exchange techniques can be used to prepare the various salts of the invention, where such techniques are well known in the art. For example, hydrochloric acid may be added to a neutral compound of the invention to prepare the hydrochloride salt thereof. Dialysis techniques may also be employed effect ion exchange and so obtain a desired salt of the invention from another salt of the invention.

The isolation and synthesis procedures described herein, especially when taken with the general knowledge in the art, provide sufficient guidance to those of ordinary skill in the art to perform the synthesis, isolation, and purification of the compounds described herein and other analogous compounds. Individual enantiomers may be obtained, if desired, from mixtures of the different forms by known methods of resolution, such as the formation of diastereomers, followed by recrystallisation. Alternatively, isomerically pure starting materials may be employed in the synthesis of a compound of the invention or various diastereomers may be separated by chromatography.

Peptides of this invention have utility as antibiotics, and may be used and administered in a manner analogous to antibiotics (particularly antibiotic peptides) known in the art, to provide the beneficial effects desired of antibiotics. The modified linear peptides of the invention may be used against gram negative and gram positive bacteria, but are particularly effective against gram-positive bacterial including *Staphylococcus aureus* and *Enterococcus faecalis*.

In using a peptide of this invention, the peptide is preferably administered to a patient in a pharmaceutical (including veterinary) composition comprising a pharmaceutically acceptable carrier, and optionally, one or more other biologically active ingredients. Such compositions may be in any form used for oral, topical, vaginal, parenteral, rectal and inhalatory application. The compositions may be provided in discrete dose units. The carriers may be particulate, with compositions being, for example, tablets or powders, or liquid, with the compositions being for example, oral syrups or injectable liquids, or gaseous, for inhalatory application.

For oral administration, an excipient and/or binder may be present. Examples are sucrose, kaolin, glycerin, starch destrins, sodium alginate, carboxymethylcellulose and ethyl cellulose. Coloring and/or flavoring agents may be present. A coating shell may be employed. For rectal administration oleaginous bases may be employed, for example, lanolin or cocoa butter. For an injectable formulation, buffers, stabilizers and isotonic agens may be included.

It will be evident to those of ordinary skill in the art that the optimal dosage of a peptide or pharmaceutical composition of this invention may depend on the weight and physical condition of the patient, on the severity and longevity of We illness; and on the particular form of the active ingredient, the manner of administration and the composition employed.

A peptide of this invention may be used in therapy with the peptide being bound to an agent, for example, a monoclonal or polyclonal antibody, a protein or a liposome, which assist the delivery of the peptide to the site of infection.

In a further embodiment, the present invention provides a method for the treatment of a patient afflicted with a bacterial infection comprising the administration thereto of a therapeutically effective amount of a compound or composition of this invention.

The term "therapeutically effective amount" refers to an amount which is effective, upon single or multiple dose administration to the patient, in providing relief of symptoms associated with bacterial infections. As used herein, "relief of symptoms" of a bacterial infection refers to a decrease in severity over that expected in the absence of treatment and does not necessarily indicate a total elimination or cure of the infection or condition caused thereby. In determining the therapeutically effective amount or dose, a number of factors are considered by the attending diagnostician, including, but limited to; the species of mammal; its size, age, and general health; the specific infection involved; the degree of or involvement or the severity of the infection or condition arising therefrom; the response of the individual patient; the particular compound administered; the mode of administration; the bioavailability characteristics of the preparation administered; the dose regimen selected; the use of concomitant medication; and other relevant circumstances.

As used herein, the term "patient" refers to a warm-blooded animal such as a mammal which is afflicted with a particular inflammatory disease state. It is understood that guinea pigs, dogs, cats, rats, mice, horses, cattle, sheep, and humans are examples of animals within the scope of the meaning of the term.

A therapeutically effective amount of a compound of Bogorol A is expected to vary from about 0.1 milligram per kilogram of body weight per day (mg/kg/day) to about 100 mg/kg/day. Preferred amounts are expected to vary from about 0.5 to about 10 mg/kg/day.

In effecting treatment of a patient afflicted with a condition described above, a compound or composition of this invention can be administered in any form or mode which makes the compound bioavailable in effective amounts, including oral, aerosol, and parenteral routes. For example, compounds can be administered orally. by aerosolization, subcutaneously, intramuscularly, intravenously, transdermally, intranasally, rectally, topically, and the like. Oral or aerosol administration is generally preferred. One skilled in the art of preparing formulations can readily select the proper form and mode of administration depending upon the particular characteristics of the compound selected, the condition to be treated, the stage of the condition, and other relevant circumstances. See, eg., Remington's Pharmaceutical Sciences, 18th Edition, Mack Publishing Co. (1990).

Peptides or salts of peptides of this invention can be administered alone or in the form of pharmaceutical composition in combination with pharmaceutically acceptable carriers or excipients, the proportion and nature of which are determined by the solubility and chemical properties of the compound selected, the chosen route of administration, and standard pharmaceutical practice.

In another embodiment, the present invention provides peptides or salts of peptides in admixture or otherwise in association with one or more inert carriers. These compositions are useful, for example, as assay standards, as convenient means of making bulk shipments, or as pharmaceutical compositions. An assayable amount of a compound of this invention is an amount which is readily measurable by standard assay procedures and techniques as are well known and appreciated by those skilled in the art. Assayable amounts will generally vary from about 0.001T to 75% of the composition by weight. Inert carriers can be any material which does not degrade or otherwise covalently react with the compound. Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

The pharmaceutical compositions of this invention may be prepared in manners well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, parenteral, or topical use and may be administered to the patient in the form of tablets, capsules, suppositories, solution, suspensions, or the like.

The compounds or compositions of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention. The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavours. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

Compounds or compositions of the present invention may also be administered by aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols may be delivered in single phase, bi-phasic, or tri-phasic systems in order to deliver the active ingredient. Delivery of the aerosol includes the necessary container, activators, valves, subcontainers, and the like. Preferred aerosols are able to be determined by one skilled in the art.

The compounds or compositions of this invention may also be administered topically, and when done so the carrier may suitably comprise a solution, ointment or gel base. The base, for example, may comprise one or more of the following: petrolaum, lanolin, polyethylene glycols, bee wax, mineral oil, diluents such as water and alcohol, and emulsifiers and stabilizers. Topical formulations may contain a concentration of the compound of this invnention of from about 0.1 to about 10% w/v (weight per unit volume).

Solutions or suspensions according to this invention may also include one or more of the following adjuvants: sterile diluents such as water for injection, saline solution, fixed oils, polyethylene glycols, glycerin, propylene glycol or other synthetic solvents, antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of toxicity such as sodium chloride or dextrose. The parenteral preparation can be enclosed in ampoules, disposable syringes or multiple dose vials made of glass or plastic.

Peptides or peptide salts of the invention may be combined with one or more known antibiotics to provide a composition having a particularly desired efficacy.

The following examples are offered by way of illustration and not by way of limitation.

EXAMPLES

Symbols and abbreviations used herein are in accordance with the recommendation of IUPAC-IUB Commissioner on Biochemical Nomenclature, *J. Biol. Chem.* 1971, 247, 977. Abbreviations: "bp" refers to boiling point; BOP= benzotriazol-1-yl-oxy-tris-(dimethylamino) phosphonium hexafluorophosphate; "BrZ" refers to bromobenzyloxycarbonyl; "Bzl" refers to benzyl; "°C." refers to degrees Celsius; "DCC" referes to N,N-dicyclohexylcarbodiimide; DCM dichloromethane; DIEA=N,N-diisopropylethylamine; DMF=N,N-dimethylformamide; "DPPA" refers to diphenylphosphorylazide; FAR-MS=fast atom bombardment mass spectrometry; "HOBt" refers to 1-hydroxybenzotriazole; "g" refers to grams; "Leu" refers to leucine; "mL" refers to milliliters; "mm Hg" refers to millimeters of mercury; "mmol" refers to millimoles; "NMP" refers to N-methylpyrrolidone; "Orn" refers to ornithine; "TEA" refers to triethylamine; TMSOTf= trimethylsilyl trifluoromethanesulfonate; "Tos" refers to p-toluenesulfonyl; "Trp" refers to tryptophan; "Tyr" refers to tyrosine; "Val" refers to valine, Z=benzyloxycarbonyl; "mg" refers to micrograms; "mL" refers to microliters; and "mM" refers to micromolar.

A. PREPARATIVE EXAMPLES

Example A1

Bogorol A may be isolated after fermentation of ATCC 55797 as described below. The marine bacterial isolate MK-PNG-276A, tentatively identified as a *Bacillus laterosporus* by MIDI analysis of cellular fatty acids, was obtained from the tissues of an unidentified tube worm collected at −15 m off of Lolata Island, Papua New Guinea. MK-PNG-276A has been deposited with the American Type Culture Collection as ATCC 55797.

MK-PNG-276A was cultured on trays of solid tryptic soy agar supplemented with NaCl to concentrations of 1%. Twenty-one 400 mL agar trays (9"×15") were cultured for five days after which the combined cells and agar were lyophilized. The dry cells were scrapped off the agar (21.5 g) and extracted with MeOH (500 mL) three times over a period of one week. The methanolic extract was combined, filtered, and reduced in vacuo to give a brown/gray tar. The tar was taken up in 250 mL H20/MeOH (4:1) and partitioned with 100% EtOAc (3×250 mL), the combined EtOAc extracts were reduced in vacuo to give a taupe/brown crystalline solid (6.5 g). In two portions, this extract was subjected to size-exclusion chromatography on a Sephadex LH-20 (100% MeOR) column to give 500 mg of a fast eluting ninhydrin positive fraction (Rf=0 on reversed-phase TLC (100% MeOH)) which showed broad spectrum antibiotic activity. This fraction was loaded onto a reversed-phase 10 g Sep-Pak, previously equilibrated with 100% water, by dissolving the sample in a minimum of quantity of MeOH. Upon addition to the top of the column an equivalent volume of water was added, precipitating the active component. The column was flushed first with 50 mL 100% $H_2O$ which was subsequently discarded, followed by 100 mL of 60% $H_2O$ (0.2% TFA) 40% MeCN which gave 90 mg of a mixture of large molecular weight peptides (1556-1618 Da.) as indicated by LRFABMS, which were responsible for the broad spectrum antibiotic activity. This process was repeated until approximately 2.0 g of crude peptide was obtained. 1.5 g of the crude was further separated into nine fractions (A–I) by reversed-phase HPLC on a dual pump Waters 486 TAD chromatograph using a Rainin Dynamax-60 C18 column, eluting with 60% $H_2O$ (0.2% TFA) 40% MeCN. The nine fractions collected were shown to be of the same peptide family by LRFABMS and 1H NMR. Fraction E, which contained Bogorol A, was prioritized due to its potent antimicrobial profile.

Bogorol A gave a [M+H]+ ion in the HRFABMS at m/z 1584.08500 appropriate for a molecular formula of $C_8OH_{142}O_{16}N_{16}$. Detailed analysis of the 500 MHz 1H, 13C, COSY, HOHAHA, HMQC, HMBC and ROESY data for Bogorol A led to the following partial structures.

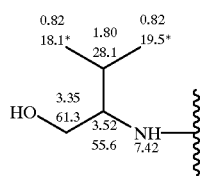

VOL: Valinol or
2-amino-3-methyl-1-butanol

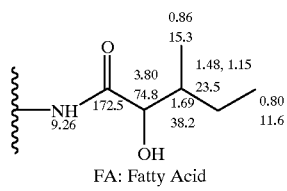

FA: Fatty Acid

*Assignments interchangeable

Hydrolysis of Bogorol A (1) at 100° C. with 6N HCl and examination of the pentafluropropionamide isopropyl ester derivatives of the liberated amino acids via chiral GC analysis confirmed the presence of L-valine, L-leucine, D-leucine, L-isoleucine, D-tyrosine, L-lysine, D-lysine, and D-ornithine. Bogorol A was converted into its hexaacetate derivative (5), and NMR data was acquired at 800 MHz.

Crude Bogorol A. (50 mg) was acetylated in a 3:1 mixture of anhydrous pyridine and acetic anhydride at room temperature for 16 hours. Solvent was removed in vacuo and the resulting solids were chromatographed on a reversed-phase silica Sep-Pak™(2 g) eluting with a gradient of 100% H2O-100% MeOH. The fractions ($^{30}/_{70}$ through $^{10}/_{90}$) were reduced in vacuo and further purified by reversed-phase HPLC (50/50 H2O/MeCN) yielding 16 mg hexaacetyl-bogorol (5).

TABLE 1

1H NMR Data (800 MHz) for Hexaacetylbogorol (5) (DMSO-D6)

| Res. | | $\delta^1H$ | Res. | | $\delta^1H$ |
|---|---|---|---|---|---|
| VOL-OAc[A,B] | CH₃ Acetate | 2.07 | LYS- | δCH₂ | 1.34 |
| | CO Acetate | — | NAc2 | εCH₂ | 2.94 |
| | NH | 7.76 | | NH | 7.73 |
| | αCH | 3.7 | | CO | — |
| | βCH₂ | 4.10, 3.85 | VAL2 | NH | 7.76 |
| | βCH | 1.76 | | αCH | 4.18 |
| | γCH₃x2[E] | 0.86 | | βCH | 1.97 |
| LEU1 | NH | 8.14 | | γCH₃x2[E] | 0.84 |
| | αCH | 4.28 | | CO | — |
| | βCH₂ | 1.41, 1.36 | VAL3 | NH | 7.90 |
| | γCH | 1.36 | | αCH | 4.17 |
| | δCH₃x2[E] | 0.81, 0.77 | | βCH | 1.94 |
| | CO | — | | γCH₃x2[E] | 0.81 |
| TYR-OAc | CH₃ Acetate | 2.22 | | CO | — |
| | CO Acetate | — | ILE | NH | 7.67 |
| | NH | 8.20 | | αCH | 4.24 |
| | αCH | 4.57 | | βCH | 1.74 |

Hexaacetylbogorol A (5)

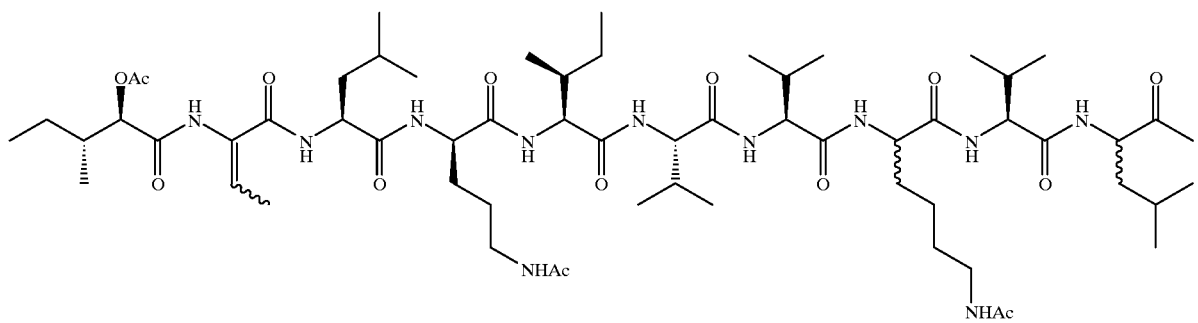

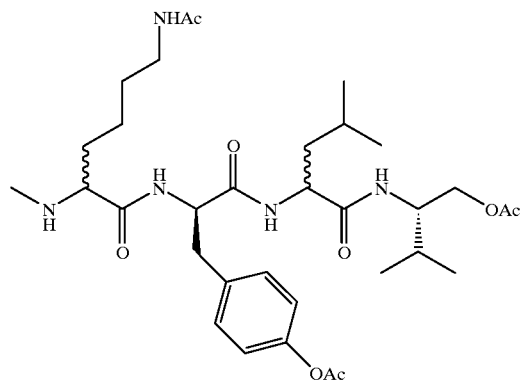

TABLE 1-continued

1H NMR Data (800 MHz) for Hexaacetylbogorol (5) (DMSO-D6)

| Res. | | δ¹H | Res. | | δ¹H |
|---|---|---|---|---|---|
| | βCH$_2$ | 2.96, 2.75 | | γCH$_3$$^E$ | 0.88 |
| | iC | — | | γCH$_2$ | 1.36, 1.0 |
| | oCH | 7.24 | | δCH$_3$ | 0.75 |
| | mCH | 6.96 | | CO | — |
| | pCH | — | ORN-NAc | CH$_2$ Acetate | 1.76 |
| | CO | — | | CO Acetate | — |
| LYS-NAc1 | CH$_2$ Acetate | 1.76 | | NH | 7.98 |
| | CO Acetate | — | | αCH | 4.30 |
| | NH | 7.91 | | βCH$_2$ | 1.62, 1.56 |
| | αCH | 4.20 | | γCH$_2$ | 1.39, 1.33 |
| | βCH$_2$ | 1.28, 1.38 | | δCH$_2$ | 2.96 |
| | γCH$_2$ | 0.99 | | NH | 7.75 |
| | δCH$_2$ | 1.24 | | CO | — |
| | εCH$_2$ | 2.92 | LEU3 | NH | 7.89 |
| | NH | 7.67 | | αCH | 4.31 |
| | CO | — | | βCH$_2$ | 1.50 |
| LEU2 | NH | 8.04 | | γCH | 1.62 |
| | αCH | 4.29 | | δCH$_3$x2$^E$ | 0.86, 0.84 |
| | βCH$_2$ | 1.43 | | CO | — |
| | γCH | 1.53 | DHB$^C$ | NH | 9.57 |
| | δCH$_2$x2$^E$ | 0.86, 0.84 | | αC | — |
| | CO | — | | βCH | 5.63 |
| VAL1 | NH | 7.75 | | γCH$_3$ | 1.76 |
| | αCH | 4.17 | | CO | — |
| | βCH | 1.97 | FA-OAc$^D$ | CH$_2$ Acetate | 1.94 |
| | γCH$_2$x2$^E$ | 0.79 | | CO Acetate | — |
| | CO | — | | αCH | 4.73 |
| LYS-NAc2 | CH$_2$ Acetate | 1.76 | | βCH | 1.84 |
| | CO Acetate | — | | γCH$_3$$^E$ | 0.89 |
| | NH | 7.96 | | γCH$_2$ | 1.40, 1.14 |
| | αCH | 4.28 | | δCH$_3$ | 0.84 |
| | βCH$_2$ | 1.63, 1.48 | | CO | — |
| | γCH$_2$ | 1.24, 1.20 | | | |

$^A$VOL represents the residue valinol or 2-amino 3-methyl 1-butanol.
$^B$Ac represents the acetate of the corresponding residue, i.e. TYR-OAc is Tyrosine Acetate.
$^C$Dhb is dehydrobutyrene or 2-amino butenoic acid.
$^D$FA is the Fatty Acid residue, 2-hydroxy,3-methyl pentanoic acid.
$^E$Protein assignment in the methyl region was assigned by inspection of 2D NMR.

Hexaacetylbogorol A (5) gave a [M+H]+ ion in the HRFABMS at m/z 1837.15212 appropriate for a molecular formula of $C_{92}H_{155}O_{22}N_{16}$, and suitable for the addition of six acetate unites to Bogorol A. Detailed analysis of the 800 MHz NMR data resulted in the assignment of all the component amino acids (Table 1), the connectivity of which were defined by key NOESY correlations (Table 2). The connectivity was further supported by fragmentation patterns in the LRFABMS of the hexaacetyl derivative 5 (Table 3).

TABLE 2

| Amino Acid NH (ppm) | Tabulated NOESY Correlations | |
|---|---|---|
| | NH Correlations (ppm) | αCH Correlations (ppm) |
| VOL (7.76) | LEU1 (8.14) | VOL (3.78); LEU1 (4.28) |
| LEU1 (8.14) | VOL (7.76); TYR (8.20) | LEU1 (4.28); TYR (4.57) |
| TYR (8.20) | LEU1 (8.14); LYS1 (7.91) | TYR (4.57); LYS1 (4.20) |
| LYS1 (7.91) | TYR (8.20); LEU2 (8.04) | LYS1 (4.20); LEU2 (4.29) |
| LEU2 (8.04) | LYS1 (7.91); VAL1 (7.75) | LEU2 (4.29); VAL1 (4.17) |
| VAL1 (7.75) | LEU2 (8.04); LYS2 (7.96) | VAL1 (4.17); LYS2 (4.28) |
| LYS2 (7.96) | VAL1 (7.75); VAL2 (7.76) | LYS2 (4.28); VAL2 (4.18) |
| VAL2 (7.76) | LYS2 (7.96); VAL3 (7.90) | VAL2 (4.18); VAL3 (4.17) |
| VAL3 (7.90) | VAL2 (7.76); ILE (7.67) | VAL3 (4.17); ILE (4.24) |
| ILE (7.67) | VAL3 (7.90); ORN (7.98) | ILE (4.24); ORN (4.30) |
| ORN (7.98) | ILE (7.67); LEU3 (7.89) | ORN (4.30); LEU3 (4.31) |
| LEU3 (7.89) | ORN (7.98); DHB (9.57) | LEU3 (4.31) |
| DHB (9.57) | LEU3 (7.89) | FA (4.73) |

TABLE 3
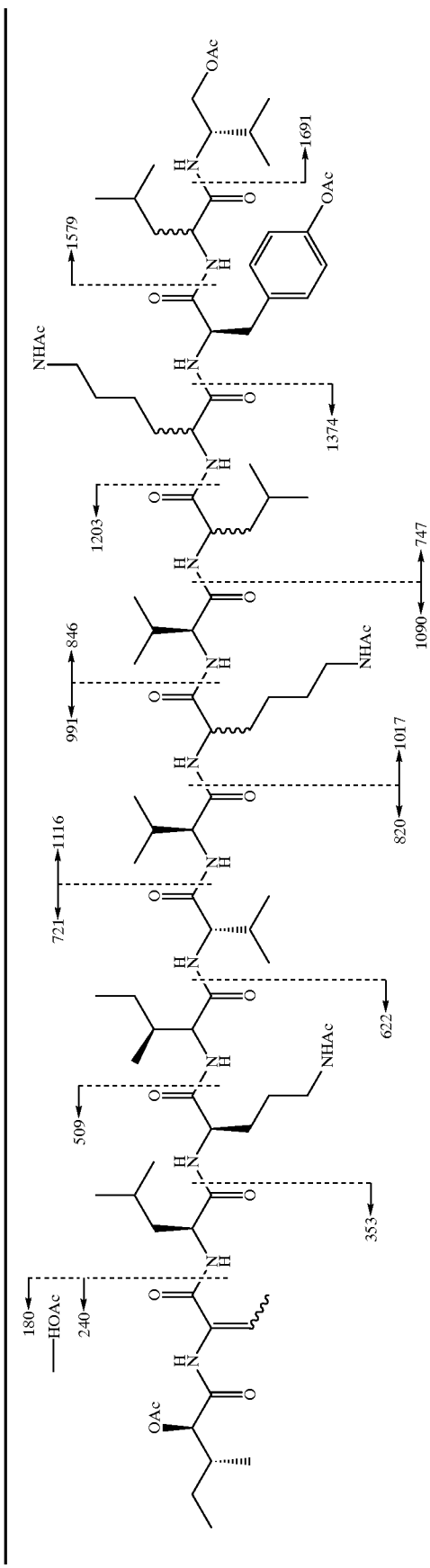
LRFABMS Fragmentation Summary of 5
| [Fragment Ion]+ | Residue Cleaved | LRFABMS Unit Mass Observed | Fragment Mass Calculated |
|---|---|---|---|
| $NaC_{12}H_{184}O_{22}N_{16}$ | — | 1859 | 1836.1500 |
| $C_{92}H_{155}O_{22}N_{16}$ | VOL-OAc | 1837 | 1691.0400 |
| $C_{85}H_{140}O_{20}N_{15}$ | LEU/ILE | 1691 | 1577.9560 |
| $C_{79}H_{129}O_{19}N_{14}$ | TYR-OAc | 1579 | 1372.8820 |
| $C_{68}H_{118}O_{16}N_{13}$ | LYS-NAc | 1374 | 1202.7760 |
| $C_{60}H_{104}O_{14}N_{11}$ | LEU/ILE | 1203 | 1089.6925 |
| $C_{54}H_{95}O_{13}N_{10}$ | VAL | 1090 | 990.6240 |
| $C_{49}H_{84}O_{12}N_9$ | LYS-NAc | 991 | 820.5184 |
| $C_{41}H_{70}O_{10}N_7$ | VAL | 820 | 721.4500 |
| $C_{36}H_{61}O_9N_6$ | VAL | 721 | 622.3816 |
| $C_{31}H_{52}O_8N_5$ | LEU/ILE | 622 | |

TABLE 3-continued

LRFABMS Fragmentation Summary of 5

| [Fragment Ion]+ | Residue Cleaved | LRFABMS Unit Mass Observed | Fragment Mass Calculated |
|---|---|---|---|
| $C_{25}H_{41}O_7N_4$ | ORN-NAc | 509 | 509.2975 |
| $C_{18}H_{28}O_5N_3$ | LEU/ILE | 353 | 353.2076 |
| $C_{12}H_{18}O_4N$ | DHB | 240 | 240.1236 |
| $C_9H_{13}O_3$ | — | 157 | 157.0865 |

For Table 3, the program MMCALC was used to calculate mass.

The amino acid sequence of (5) was determined by analysis of NOESY data. LRFABMS supported the amino acid sequence derived from the NMR data. The NMR data assigned three LEU residues and one ILE, the positioning of the ILE residue was determined by NOESY data. The LRFABMS data was consistent with initial cleavage of the amide linkage of VOL-OAc/LEU bond followed by the sequential loses summarized in Table 3 above.

Bogorls B, C, and D and other antibiotic analogs of Bogorol A that fall within this invention can also be obtained from the crude culture extract described above.

Example A2

Fermentation techniques with the microorganism ATCC 55797 may be used to obtain Bogorols A-D as described in Example A1. Thereafter, these peptides may be derivatized to form salts (either acid- or base-addition salts, depending on whether the amino acid sidechain is basic or acidic, respectively), esters (from amino acid sidechains containing a carboxylic acid croup), amines (from amino acid sidechains containing an amino group), ether (from amino acid sidechains containing an hydroxyl group) and amides (from amino acid sidechains containing either and amine or carboxylic acid group) of the invention.

Example A3

Precursor directed biosynthesis, wherein a culture media containing the microorganism isolated in Example A1 is supplemented with a replacement amino acid at fairly high concentrations, may be used to prepare modified linear peptides of the invention. See, e.g., Katz E. and Demain, A. L., "The Peptide Antibiotics of Bacillus: Chemistry Biogenesis, and Possible Functions," *Bacteriological Reviews*, Jun. 1977, pp. 449–474.

The culture media described in Example A1 can be employed in precursor directed biosynthesis to prepare the analogs of Bogorols A-D by providing the microorganism ATCC 55707 fairly high concentrations of the following amino acids: butyrine may replace valine. L-diaminobutyric acid may replace ornithine and/or lysine; any of L-isoleucine, L-alloisoleucine, L-norvaline, L-cyclopropylalanine and norleucine may replace leucine or isoleucine: any p-fluorophenylalanine, tryptophan and thienylalanine may replace tyrosine.

Synthesis of of Bogorol A and Analogs

Solution phase techniques as set forth in K. Okamato, K. et al, *Bull. Chem. Soc. Jpn.* 50:231–236 (1977), Ohno, M. et al. *J. Am. Chem. Soc.* 88(2):376–377 and Kosui, N. et al. *Int. J. Peptide Protein Res.* 18:127–134 (1981) may be modified to prepare the modified linear peptides of the present invention, merely by appropriate substitution of the suitably protected amino acids, carboxyl reduced amino acids, or α-hydroxy acids.

The following examples present typical syntheses. These examples are understood to be illustrative only and are not intended to limit the scope of the present invention in any way.

Example A4

The p-nitrobenzophenone oxime polymer described by DeGrado and Kaiser may be used as a solid support in preparing modified linear peptides represented by formlae (A) and (B) of the present invention. See DeGrado, W. F.; Kaiser, E. T., *J. Org. Chem.* 45:1295–1300 (1980). The first step would involve synthesis of a linear peptide comprising residues AA2 to AA13. For the preparation of, for example, Bogorol A the starting compound Boc-Leu-resin is the same as described in the Osapay article, and the excess oxime groups may be capped by acetylation as described therein. The peptide chain may be assembled by the appropriate sequential addition of the following Na-Boc-amino acids, which have the required configuration: BocLeuOH, BocOrn (Z)OH, BocValOH, BocTyr(2,6-C12-Bzl)OH, BocLys(Z)OH, BocILeOH, BocdehydrobutyrineOH, Trimethylsilyl-2-hydroxy-3-methylpentaonoic acid, all according to the BOP peptide coupling procedure of Fournier, A.; Wang, C. T.; Felix, A. M., *Int. J. Pept., Prot. Res.*, 31:86–97 (1988). N-Boc(OHBn)ThrOH can act as a protected dehydrobutyrine residue in both solution and solid phase synthesis of Bogorol A as detailed in Valentekovich, R. J.; Schreiber, S. L. *J. Amer. Chem. Soc.* 1995, 117, 9069–9070 and Bauer, S. M,; Armstrong, R. W. *J. Amer. Chem. Soc.* 1999, 121, 6355–6366.

Boc protecting groups may be removed by treatment with 25% TFA/DCM solution for 30 minutes. After the appropriate washing steps, Boc-amino acids and BOP reagent may be added in 5-fold excess in DMF solution followed by the same excess of DIEA. After a 2-hour reaction time, the completeness of each coupling may be monitored by the Kaiser test. See Kaiser, E.; Colescott, R. L.; Cook, P. I.,*Anal Biochem.*, 34:595–598 (1970).

Once a linear peptide N-capped with an OH protected α-hydroxy-3-methylpentanoic acid residue has been prepared, the final step would be adding a suitably derivatized valinol residue to the carboxy terminal end using BOP coupling procedures.

Protecting groups of the peptide may be removed with TMSOTf in TFA in the presence of thioanisole, according to the procdure of Fujii, N. et al., *J. Chem. Soc., Chem. Commun.*, 274–275 (1987). Hydrolysis of the partly silylated product by NH4OH may be followed by gel permeation chromatography, for example, using Sephadex G10 column (eluent, e.g.,: 2 M acetic acid in H20/ MeOH, 4/1 [v/v]). Final purification may be carried out by RP-HPLC on, for example, a Vydac C18 Proteins semi-preparative column eluted at, e.g., 4 mL/min with a linear gradient of 25%–80% acetonitrile in 0.1% (v/v) TPA over 45 minutes.

In the above-described synthesis, one or more of the Nα-Boc-amino acid starting materials may be purchased from chemical supply houses, for example, Sigma Chemical Company, P.O. Box 14508, St. Louis, Mo. 63178 (Sigma's "Peptides and Amino Acids" catalog provides a convenient listing) and Bachem, 6868 Nancy Ridge Dr., San Diego, Calif. 92121.

Example A5

Solid phase peptide synthesis according to the method originally described by Merrifield, *J. AM. Chem. Soc.* 85:2149–2154, 1963, may be used to prepare the modified linear peptides of the invention. Alternatively, solution synthesis may be used to prepare these linear peptide analogs. Generally, peptides may be elongated by deprotecting the α-amine of the C-terminal residue and coupling the next suitably protected amino acid through a peptide linkage using the methods described. This deprotection and coupling procedure is repeated until the desired sequence is obtained. This coupling can be performed with the constituent amino acids in stepwise fashion, or by condensation of fragments (two to several amino acids), or combination of both processes, or by solid phase peptide synthesis as stated above.

When a solid phase synthetic approach is employed, the C-terminal carboxylic acid is attached to an insoluble carrier (e.g. polystyrene). These insoluble carriers contain a group which will react with the a-carboxyl group to form a bond which is stable to the eolongation conditions but readily cleaved later. Examples of which include: chloro- or bromomethyl resin, hydroxymethyl resin, and aminomethyl resin. Many of these resins are commercially from Sigma Chemical Company and Bachem.

Alternatively, compounds of the invention can be synthesized using automated peptide synthesizing equipment. In addition to the foregoing, peptide synthesis methods are described in Stewart and Young, "Solid Phase Peptide Synthesis," 2nd ed., Pierce Chemical Co., Rockford, Ill. (1984); Gross Meienhofer, Udenfriend, Eds., "The Peptides: Analysis, Synthesis, Biology," Vol. 1, 2, 3, 5 and 9, Academic Press, New York, 1980–1987; Bodanszky, "Peptide Chemistry: A Practical Textbook," Springer-Verlag, New York (1988); and Bodanszky et al., "The practice of Peptide Synthesis," Springer-Verlag, New York (1984).

Coupling between two amino acids, an amino acid and a peptide, or two peptide fragments can be carried out using standard coupling procedures such as the azide method, mixed carbonic acid anhydride (isobutyl chloroformate) method, carbodiimide) method, active ester (p-nitrophenyl ester, N-hydroxy-succinic imido ester) methods, Woodward reagent K method, carbonyldiimidazole method, phosphorus reagents such as BOP-Cl, or oxidation-reduction methods. Some of these methods (especially the carbodiimide method) can be enhanced by adding 1-hydroxybenzotriazole. These coupling reactions can be performed in either solution (liquid phase) or solid phase.

The functional groups of the constituent amino acids must be protected during the coupling reactions to avoid formation of undesired bonds. The protecting groups that can be used are listed in Greene, "Protective Groups in Organic Chemistry," John Wiley & Sons, New York (1981) and "The Peptides: Analysis, Synthesis, Biology," Vol. 3, Academic Press, New York (1981). N-Boc(OHBn)ThrOH can act as a protected dehydrobutyrine residue in both solution and solid phase synthesis of Bogorol A as detailed in Valentekovich, R. J.; Schreiber, S. L. *J. Amer. Chem. Soc.* 1995, 117, 9069–9070 and Bauer, S. M.; Armstrong, R. W. *J. Amer. Chem. Soc.* 1999, 121, 6355–6366.

The α-carboxyl group of the C-terminal residue may be protected by an ester that can be cleaved to give the carboxylic acid. Protecting groups which can be used include: (1) alkyl esters such as methyl and t-butyl, (2) aryl esters such as benzyl and substituted benzyl, or (3) esters which can be cleaved by mild base treatment or mild reductive means such as trichloroethyl and phenacyl esters.

The α-amino group of each amino acid must be protected. Any protecting group known in the art can be used. Examples of which include: (1) acyl types such as formyl, trifluoroacetyl, phthalyl, and p-toluenesulfonyl; (2) aromatic carbamate types such as benzyloxycarbonyl (Cbz or Z) and substituted benzyloxycarbonyls, 1-(p-biphenyl)-1, -methylethoxy-carbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; and (7) thiol containing types such as phenylthiocarbonyl and dithiasuccinoyl. The preferred a-amino protecting group is either Boc or Fmoc, preferably Fmoc. Many amino acid derivatives suitably protected for peptide synthesis are commercially available.

The α-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidine in dimethylformamide, but any secondary amine or aqueous basic solutions can be used. The deprotection is typically carried out at a temperature between 0° C. and room temperature.

Amino acid bearing sidechain functionalities may be protected during the preparation of the peptide using any of the above-described groups. Those skilled in the art will appreciate that the selection and use of appropriate protecting groups for these sidechain functionalities depends upon the amino acid and presence of other protecting groups in the peptide. The selection of such protecting groups is important in that it should not be removed during the deprotection and coupling of the a-amino group. For example, when Boc is used as the α-amino protecting group, p-toluenesulfonyl (tosyl) moieties can be used to protect the amino sidechain of Orn. When Fmoc is chosen for the α-amine protection usually tert-butyl based protecting groups are acceptable. For instance, Boc can be used for ornithine.

Once the elongation of the peptide is completed all of the protecting groups are removed. When a solution phase synthesis is used, the protecting groups are removed in whatever manner is dictated by the choice of protecting groups. These procedures are well known to those skilled in the art.

When a solid phase synthesis is used, the peptide is cleaved from the resin, often simultaneously with protecting group removal. When the Boc protection scheme is used in the synthesis, treatment with anhydrous HF containing additives such as dimethy sulfide, anisole, thioanisole, or p-cresol at 0° C. is a preferred method for cleaving the peptide from the resin. The cleavage of the peptide can also be accomplished by other acidic reagents such as trifluoromethanesulfonic acid/trifluoroacetic acid mixtures. If the Fmoc protection scheme is used, the N-terminal Fmoc is cleaved with reagents described earlier. The other protecting groups and the peptide are cleaved from the resin using a solution of trifluoroacetic acid and various additives such as anisole.

Example A5a

Synthesis of the Linear Peptide

The linear peptide of Bogorol A may be synthesized by standard solid phase methods using an Applied Biosystems (850 Lincoln Centre Dr., Foster City, Calif.) 430A automated peptide synthesizer and protocols supplied by the manufacturer. Commercially available Boc-amino acids may be used with the following sidechain protection: Orn/Lys(Tos), Tyr(BrZ). Commercially available Boc-Val-PAM resin (0.5 mmol, Applied Biosystems) may be deprotected with trifluoroacetic acid (2% anisole) and coupled in NMP with the HOBt esters of Boc-amino acids (4 equivalents). The HOBt esters of Boc-amino acids may be formed by the reaction of the Boc-amino acid with DCC and HOBt. N-Boc(OHBn)ThrOH can act as a protected dehydrobutyrine residue in both solution and solid phase synthesis as detailed in Valentekovich, R. J.; Schreiber, S. L. *J. Amer. Chem. Soc.* 1995, 117, 9069–9070 and Bauer, S. M.; Armstrong, R. W. . *J. Amer. Chem. Soc.* 1999, 121, 6355–6366.

Couplings may be carried out for 30 minutes and the resin subsequently washed with NMP and DCM. Any unreacted amine may be acylated with acetic anhydride. The deprotection and coupling may be repeated until complete assembly of the protected peptide resin is achieved. The linear peptide may be simultaneously deprotected and removed from the resin with anhydrous hydrogen fluoride (10 mL) at 0° C. for 30 minutes in the presence of anisole (5%). The peptide may then be extracted with 50% acetic acid, water and aqueous acetonitrile, and lyophilized. The final step in the synthesis would be coupling of valinol with the linear peptide.

Example A5b

All procedures are carried out in dry glassware under argon. Aldrich Chemical's anhydrous sure-seal bottled piperidine, pyridine, DIPEA, DCM, DMF and THF were used where appropriate. (2R, 3R)-HMVA (hydroxymethylvaleric acid) and (2R, 3S)-HMVA were purchased from Sigma as the sodium salts of D-2-hydroxy-3-methyl-valeric acid and D-allo-2-hydroxy-3-methyl-valeric acid respectively. PyBOP was also obtained from Sigma, while 2-ClTrt resins and Fmoc-valinol were purchased from Anaspec Inc. Automated peptide synthesis was provided by The University of British Columbia (Vancouver, Canada) Biotechnology Laboratory—NAPS Unit.

Loading 2-ClTrt resin with valinol: following the procedure set out in the Novabiochem Catalog (2000) for alcohol attachment to trityl resin, 500 mg (1.5 mmol) Fmoc-Vol-OH and 500 ml (6 mmol) pyridine was added to a slurry of 500 mg (0.7 mmol active subst.) 2-ClTrt chloride resin in 5 ml THF. The reaction mixture was heated to reflux with magnetic stirring for 4 h, then filtered and washed with 3×DCM (dichloromethane)/MeOH/DIPEA(diisopropylethylamine) (17:2:1), 3×DCM, 3×DMF(dimethylformamide) and 3×DCM. The resin is dried and, in the case of Fmoc-D-Vol-2-ClTrt, a yield of 676 mg resin with a load of 0.12 mmol/g (according to UV; Novobiochem Catalog) was obtained. Fmoc-Vol-2-ClTrt is commercially available from Anaspec with a substitution of 0.20 mmol/g. The Fmoc protecting group is removed by treating the resin with 3×20% piperidine/DMF, followed by a DMF-wash.

Synthesis: 300 mg (~0.06 mmol peptide) H2N-L-(tBu)Thr-L-Leu-D-(Boc)Orn-L-Ile-L-Val-LVal-D-(Boc)Lys-L-Val-L-Leu-L-(Boc)Lys-Val-L-Leu-L(Boc)Lys-D-(tBu)Tyr-D-Leu-L-Vol-2-ClTrt resin was prepared using commercial L-Vol-2-ClTrt resin and automated peptide synthesis. (2R, 3R)-HMVA was prepared by acidification of the corresponding sodium salt and Et2O extraction. 80 mg (0.6 mmol) (2R, 3R)-HMVA and 312 mg (0.6 mmol) PyBOP was dissolved in 4 ml DMF and added to the slurry of the loaded resin in DMF. 210 ml (1.2 mmol) DIPEA was added dropwise and the mixture was stirred for 18 h. The slurry was transferred to a glassfilter funnel, washed with 3×DMF and 3×DCM and dried prior to cleavage. The cleavage and deprotection was achieved by swirling the resin with a TFA(trifluoroacetic acid)/scavenger mix for 3 h. The cleavage mixture consists of 2.415 ml TFA, 150 ml H2O and 375 ml scavenger premix (300 mg phenol/300 ml thioanisol/150 ml 1,2-ethanedithiol). The TFA/scavenger mix was reduced under vacuum and the residual oily residue was precipitated with Et2O. 84 mg of a white powder was obtained after centrifugation and lyophilization. HPLC, 1HNMR and MS-data were consistent with the proposed structure. Further purification can be achieved by HPLC on C18 mBondapak (8×200 mm RadPak), eluting with 60:40 MeOH/H2O for 2½ ml/min. The above-described procedure is schematically shown below in Table 4.

TABLE 4

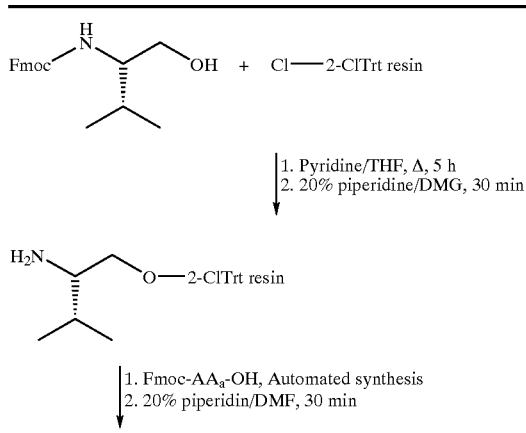

TABLE 4-continued

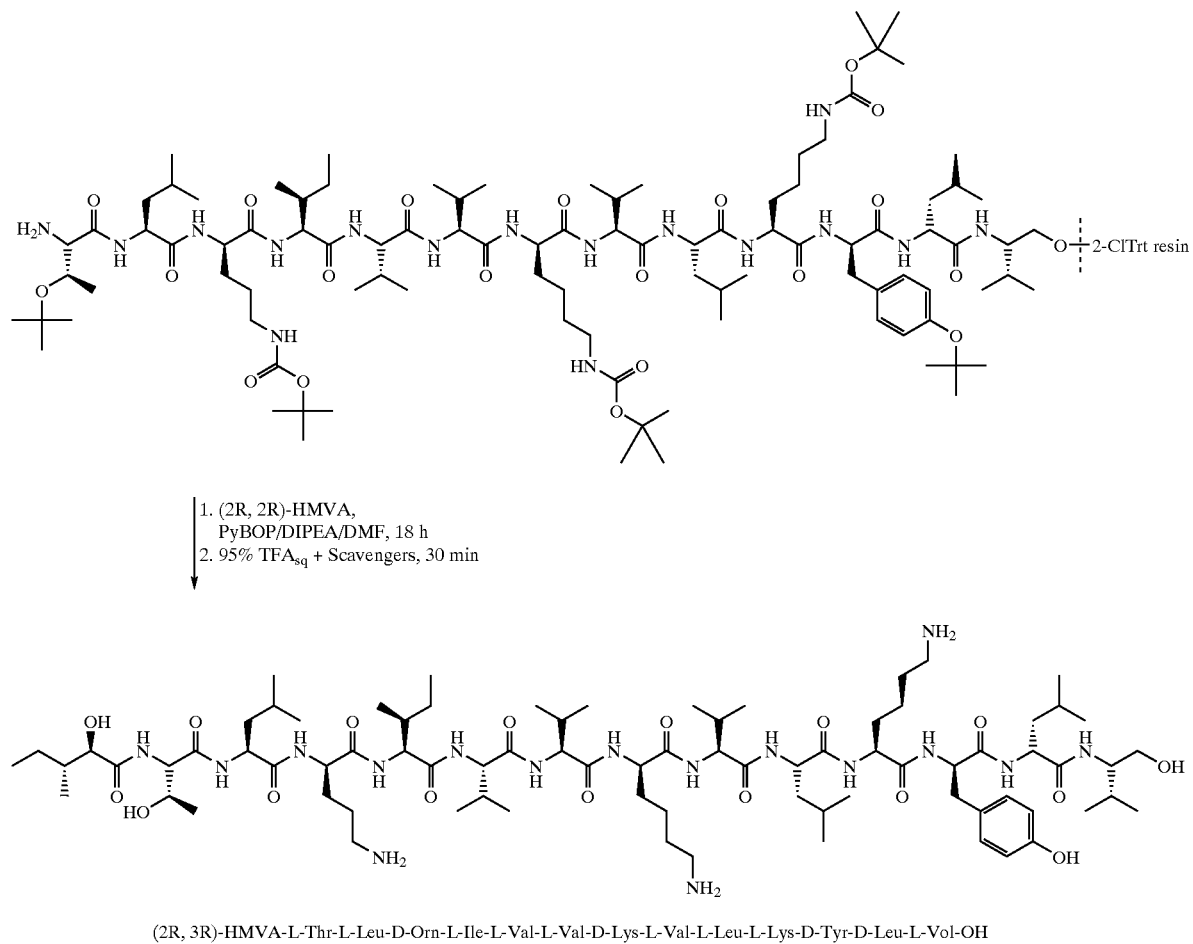

1. (2R, 2R)-HMVA, PyBOP/DIPEA/DMF, 18 h
2. 95% TFA$_{aq}$ + Scavengers, 30 min (2R, 3R)-HMVA-L-Thr-L-Leu-D-Orn-L-Ile-L-Val-L-Val-D-Lys-L-Val-L-Leu-L-Lys-D-Tyr-D-Leu-L-Vol-OH

B. ACTIVITY EXAMPLES

Example B1

In a standardized agar dilution antimicrobial assay described below, Bogorol A was found to be selectively antimicrobial, with the minimum inhibitory concentrations listed in the table below. A solution of Bogorol A was prepared by dissolving 3 mg of e compound in 300 μL of dimethylsulfoxide (DMSO). Serial two-fold dilutions were prepared in DMSO, and 50 μL of each dilution was mixed with 5 mL of melted Mueller-Hinton agar to achieve a final Bogorol A concentration range of 200 to 0.48 μg/ml. After the agar solidified, standardized suspensions of the target organisms were inoculated onto the surface of the agar using a multipoint inoculator. The standardized suspensions were prepared in tryptic soy broth adjusted to a 1.0 McFarland turbidity standard. The plates were incubated over night at 37° C. Activity of Bogorol A was indicated by a lack of growth of any target organism at its point of inoculation. The results presented in the table below indicate that Bogorol A is active against methicillin-resistant *Staphylococcus aureus* and vancomycin-resistant *Enterococcus faecalis*. The results also indicate that Bogorol A is moderately active against *Escherichia coli* and *Stenotrophomonas maltophilia*, but it is essentially inactive against the other target organisms tested.

TABLE 5

Minimal Inhibitory Concentrations of Bogorol A Against a Panel of Human Pathogens

| | |
|---|---|
| Drug Resistant *Staphylococcu aureus* | 1.56–3.13 |
| Drug Resistant *Enterococcus faecalis* | 6.25–12.5 |
| *Escherichia coli* | 25–50 |
| *Stenotrophomonas maltophilia* | 100–200 |
| *Berkholderia cepacia* | >200 |
| Drug Resistant *Pseudomonas aeruginosa* | >200 |
| *Candida aibicans* | >200 |

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the appended claims. All patents, patent applications and publications referred to herein are hereby incorporated by reference.

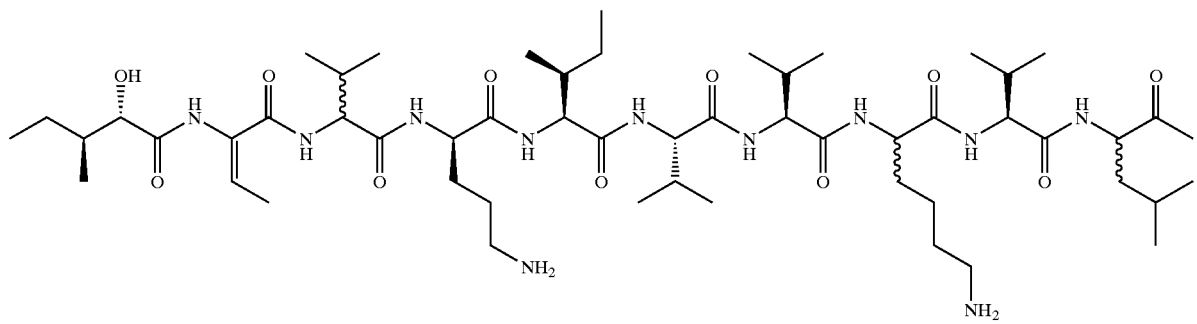

-continued
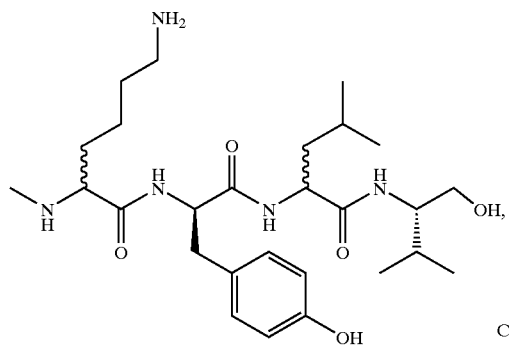
C
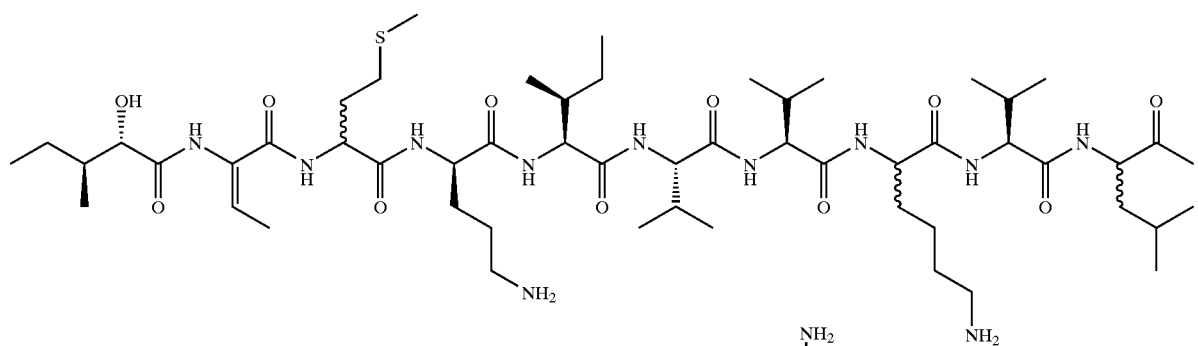
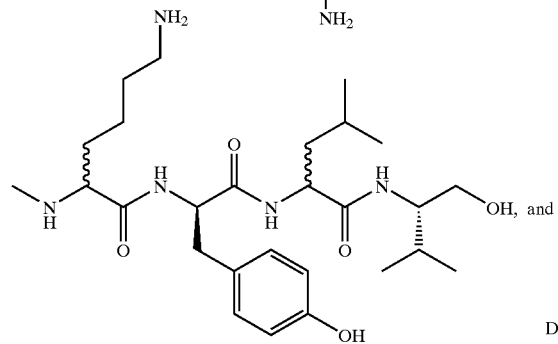
D, and
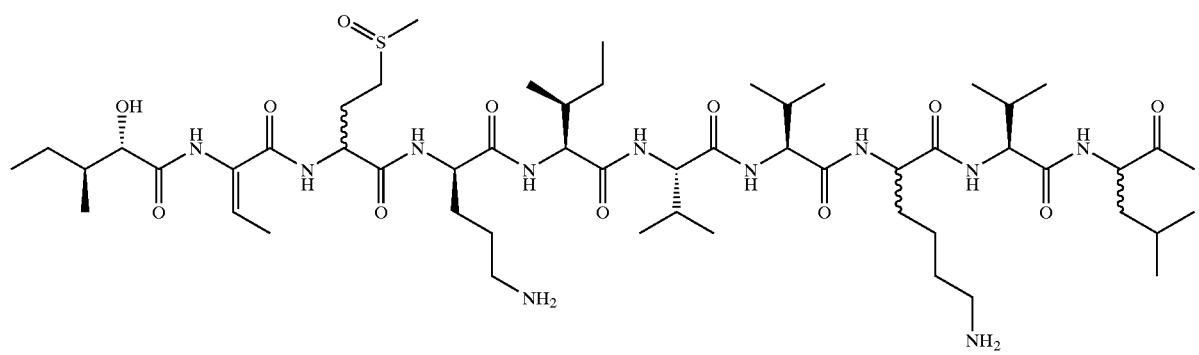
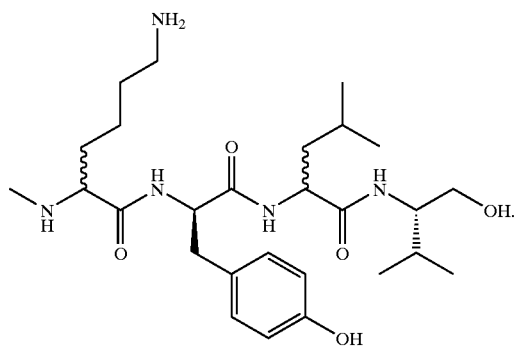

25. The composition of claim 20, wherein the peptide has the structure:
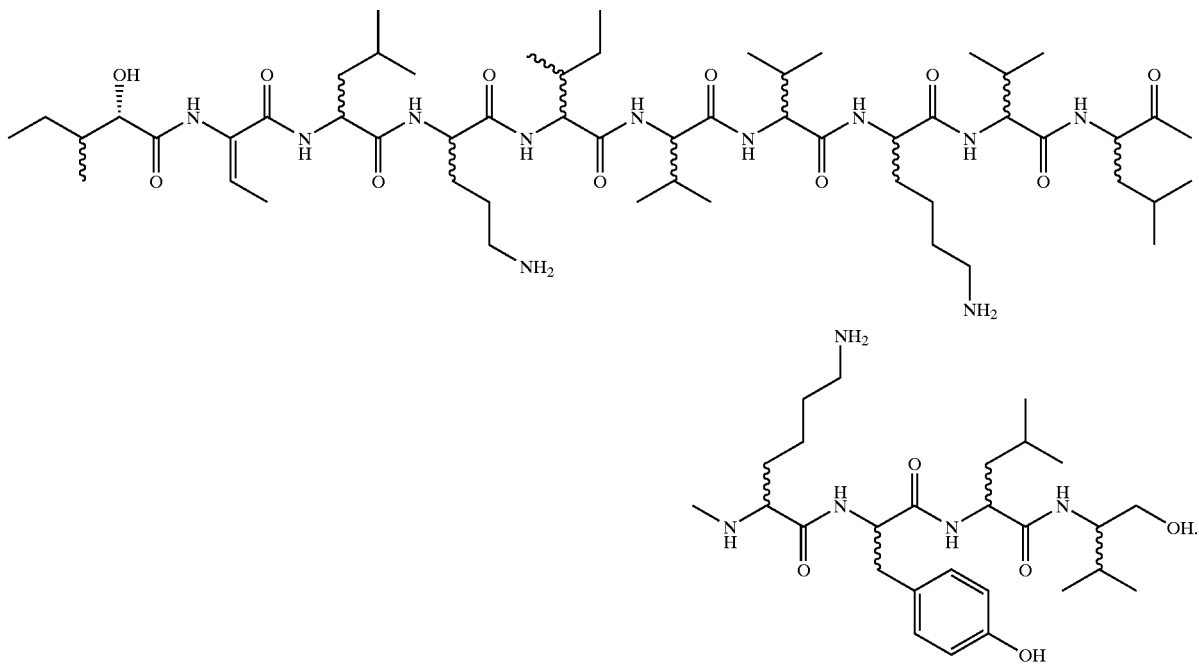

What is claimed is:

1. An isolated antibiotic peptide or salt of an antibiotic peptide of formula:

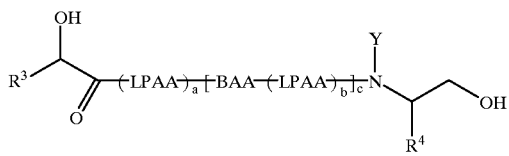

wherein:
a, b, and c are independently selected integers, wherein a=1–5, b=2–6, and c=2–5;

Y is selected from the group consisting of: H; OH; and, a linear, branched or cyclic, saturated or unsaturated alkyl of one to ten carbon atoms;

LPAA is an amino acid residue having the structure —NX—C$^\alpha$R$^1$—CO—, wherein for each LPAA in the peptide, R$^1$ is selected from the group consisting of: hydrogen; a linear, branched or cyclic, saturated or unsaturated alkyl containing one to ten carbons atoms optionally substituted with —OH, —OR, —SH, —SR, —SOCR, —NHCOR, —I, —Br, —Cl, —F, —CN, —O$_2$CR, —CO$_2$R, —CHO, —COR, —CONH$_2$, —CONHR, —CON(R)$_2$, —COSR, —SOR, or —SO$_2$R; benzyl, in which a phenyl ring of the benzyl is optionally substituted with R, —OH, —OR, —O$_2$CR, —SH, —SR, —SOCR, —NHCOR, —I, —Br, —Cl, —F, —CN, —CO$_2$R, —CHO, —COR, —CONH$_2$, —CONHR, —CON(R)$_2$, —COSR, —NO$_2$, —SOR, or —SO$_2$R; and, arylalkyl in which an alkyl group of the arylalkyl has two to ten carbon atoms and is linear, branched or cyclic, saturated or unsaturated, optionally substituted with —OH, —OR, —O$_2$CR, —SH, —SR, —SOCR, —NHCOR, —I, —Br, —Cl, —F, —CN, —CO$_2$R, —CHO, —COR, —CONH$_2$, —CONHR, —CON(R)$_2$, —COSR, —NO$_2$, —SOR, or —SO$_2$R, and in which an aryl ring of the arylalkyl is phenyl, or indole, optionally substituted with R, —OH, —OR, —O$_2$CR, —SH, —SR, —SOCR, —NHCOR, —I, —Br, —Cl, —CN, —CO$_2$R, —CHO, —COR, —CONH$_2$, —CONHR, —CON(R)$_2$, —COSR—NO$_2$, —SOR, or —SO$_2$R; wherein for R$^1$, R in a substituent is a linear, branched or cyclic, saturated or unsaturated alkyl of one to ten carbon atoms, and providing that when R$^1$ is joined to C$^\alpha$ by a single bond, H is also present joined to C$^\alpha$; and, for each LPAA in the peptide, X is selected from the group consisting of: H; OH; and, a linear, branched or cyclic, saturated or unsaturated alkyl group containing one to ten carbons;

BAA is an amino acid residue having the structure —NX—CHR$^2$—CO—, wherein for each BAA in the peptide, R$^2$ is selected from the group consisting of: a linear, branched or cyclic, saturated or unsaturated alkyl group of one to ten carbons, substituted with one of NH$_2$, NRH, N(R)$_2$, N(R)$_3$$^+$, —NH—CNH—NH$_2$, or imidazole, and optionally additionally substituted with —OH, —OR, —SR, —SOCR, —NHCOR, —I, —Br, —Cl, —F, —CN, —CO$_2$R, —CHO, —O$_2$CR, —COR, —CONH$_2$, —CONHR, —CON(R)$_2$, —COSR, —SOR, or SO$_2$R; benzyl in which a phenyl ring of the benzyl is substituted with one of NH$_2$, NRH, N(R)$_2$, or N(R)$_3$$^+$; and optionally additionally substituted with R, —OH, —OR, —O$_2$CR, —SH, —SR, —SOCR, —NHCOR, —I, —Br, —Cl, —F, —CN, —CO$_2$R, —CHO, —COR, —CONH$_2$, —CONHR, —CON(R)$_2$, —COSR, —NO$_2$, —SOR, or —SO$_2$R; arylalkyl in which an alkyl of the arylalkyl is linear, branched or cyclic, saturated or unsaturated of two to ten carbons, optionally additionally substituted with —OH, —OR, —O$_2$CR, —SH, —SR, —SOCR, —NHCOR, —I, —Br, —Cl, —F, —CN, —CO$_2$R, —CHO, —COR, —CONH$_2$, —CONHR, —CON(R)$_2$, —COSR, —NO$_2$, —SOR, or —SO$_2$R, and in which an aryl ring of the arylalkyl is phenyl substituted with one of NH$_2$, NRH, N(R)$_2$, N(R)$_3$$^+$, indole substituted with one of NH$_2$, NRH, N(R)$_2$, N(R)$_3$$^+$, pyridine, or imidazole; and wherein the aryl ring is optionally additionally substituted with R, —OH, —OR, —O$_2$CR, —SH, —SR, —SOCR, —NHCOR, —I, —Br, —Cl, —F, —CN, —CO$_2$R, —CHO, —COR, —CONH$_2$, —CONHR, —CON(R)$_2$, —COSR, —NO$_2$, —SOR, or —SO$_2$R; wherein for R$^2$, R in a substituent is a linear, branched or cyclic, saturated or unsaturated alkyl of one to ten carbon atoms and for each BAA in the peptide, X is selected from the group consisting of: H; OH; and a linear, branched or cyclic, saturated or unsaturated alkyl of one to ten carbons; and, R$^3$ and R$^4$=R$^1$, and R$^3$ and R$^4$ are the same or different.

2. The peptide or salt of claim 1, wherein R$^1$ is a linear, branched or cyclic, saturated or unsaturated alkyl of 1–10 carbon atoms wherein the alkyl is unsubstituted or is substituted with one or more substituents selected from the group consisting of: —OH, —OR, —SH, —SR, —SOCR, —NHCOR, —I, —Br, —Cl, —F, —CN, —O$_2$CR, —CO$_2$R, —CHO, —COR, —CONH$_2$, —CONHR, —CON(R)$_2$, —COSR, —SOR, and —SO$_2$R.

3. The peptide or salt of claim 1, wherein R$^1$ is benzyl in which a phenyl ring of the benzyl is unsubstituted or is substituted with one or more substituents selected from the group consisting of: R, —OH, —OR, —O$_2$CR, —SH, —SR, —SOCR, NHCOR, —I, —Br, —Cl, —F, —CN, —CO$_2$R, —CHO, —COR, —CONH$_2$, —CONHR, —CON(R)$_2$, —COSR, —NO$_2$, —SOR, and —SO$_2$R.

4. The peptide or salt of claim 1, wherein R$^1$ is arylalkyl in which an alkyl group of the arylalkyl is unsubstituted or is substituted with one or more substituents selected from the group consisting of: —OH, —OR, —O$_2$CR, —SH, —SR, —SOCR, —NHCOR, —I, —Br, —Cl, —F, —CN, —CO$_2$R, —CHO, —COR, —CONH$_2$, —CONHR, —CON(R)$_2$, —COSR, —NO$_2$, —SOR, and —SO$_2$R.

5. The peptide or salt of claim 1, wherein R$^1$ is arylalkyl in which an aryl ring of the arylalkyl is unsubstituted or is substituted with one or more substituents selected from the group of: R, —OH, —OR, —O$_2$CR, —SH, —SR, —SOCR, —NHCOR, —I, —Br, —Cl—, —F, —CN, —CO$_2$R, —CHO, —COR, —CONH$_2$, —CONHR, —CON(R)$_2$, —COSR, —NO$_2$, —SOR, and —SO$_2$R.

6. The peptide or salt of claim 1, wherein R$^2$ is a linear, branched or cyclic, saturated or unsaturated alkyl of 1–10 carbon atoms wherein the alkyl substituents are optionally additionally substituted with one or more substituents selected from the group consisting of: —OH, —OR, —SH, —SR, —SOCR, —NHCOR, —I, —Br, —Cl, —F, —CN, —O$_2$CR, —CO$_2$R, —CHO, —COR, —CONH$_2$, —CONHR, —CON(R)$_2$, —COSR, —SOR, or —SO$_2$R.

7. The peptide or salt of claim 1, wherein R$^2$ is benzyl in which a phenyl ring of the benzyl substituents are optionally additionally substituted with one or more substituents selected from the group consisting of: R, —OH, —OR, —O$_2$CR, —SH, —SR, —SOCR, —NHCOR, —I, —Br, —Cl, —F, —CN, —CO$_2$R, —CHO, —COR, —CONH$_2$, —CONHR, —CON(R)$_2$, —COSR, —NO$_2$, —SOR, or —SO$_2$R.

8. The peptide or salt of claim 1, wherein R$^2$ is arylalkyl in which an alkyl group of the arylalkyl substituents are optionally additionally substituted with one or more substituents selected from the group consisting of: —OH, —OR, —O₂CR, —SH, —SR, —SOCR, —NHCOR, —I, —Br, —Cl, —F, —CN, —CO₂R, —CHO, —COR, —CONH₂, —CONHR, —CON(R)₂, —COSR, —NO₂, —SOR, or —SO₂R.

9. The peptide or salt of claim 1, wherein R² is arylalkyl in which an aryl ring of the arylalkyl substituents are optionally additionally substituted with one or more substituents selected from the group consisting of: R, —OH, —OR, —O₂CR, —SH, —SR, —SOCR, —NHCOR, —I, —Br, —Cl, —F, —CN, —CO₂R, —CHO, —COR, —CONH₂, —CONHR, —CON(R)₂, —COSR, —NO₂, —SOR, and —SO₂R.

10. The peptide or salt of claim 1, wherein: LPAA is an amino acid selected from the group consisting of: glycine; alanine; valine; butyrine; leucine; isoleucine; asparagine; glutamine; tryptophan; tyrosine; phenylalanine; methionine; methionine sulfoxide; threonine; serine; cysteine; and α,β-unsaturated analogs of each of said amino acids except glycine; BAA is selected from the group consisting of: ornithine; lysine; histidine; and arginine; and, R³ and R⁴ are independently selected from the group consisting of: hydrogen; methyl; ethyl; n-propyl; isopropyl; n-butyl; isobutyl; sec-butyl; benzyl; and, p-hydroxybenzyl.

11. The peptide or salt of claim 1, wherein: LPAA is selected from the group consisting of: valine; leucine; isoleucine; tyrosine; phenylalanine; methionine; methionine sulfoxide; threonine; and dehydrobutyrine; BAA is selected from the group consisting of: ornithine; lysine; and arginine; and R³ and R⁴ are independently selected from the group consisting of: hydrogen; methyl; ethyl; n-propyl; isopropyl; n-butyl; isobutyl; sec-butyl; benzyl and p-hydroxybenzyl.

12. The peptide or salt of claim 1, wherein: LPAA is selected from the group consisting of: valine; leucine; isoleucine; tyrosine; phenylalanine; methionine; methionine sulfoxide; threonine; and dehydrobutyrine; BAA is selected from the group consisting of: ornithine; lysine; and arginine; and, R³ and R⁴ are independently selected from the group consisting of: isopropyl; isobutyl; and sec-butyl.

13. The peptide or salt of claim 1, wherein: a is 1–5; c is 2–5; and, b is 2–6.

14. The peptide or salt of claim 1, wherein: a is 2; c is 3; and, b is 2–3.

15. The peptide or salt of claim 1, wherein: R³=—CH(CH)₃CH₂CH₃.

16. The peptide or salt of claim 1, wherein: Y=H.

17. The peptide or salt of claim 1, wherein: R⁴=—CH(CH₃)₂.

18. The peptide or salt of claim 1, wherein the peptide is selected from the group consisting of structures A, B, C, and D:

A

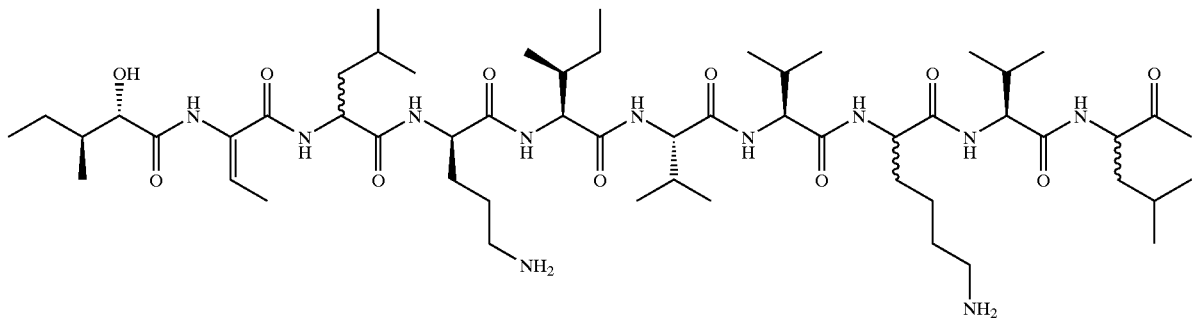

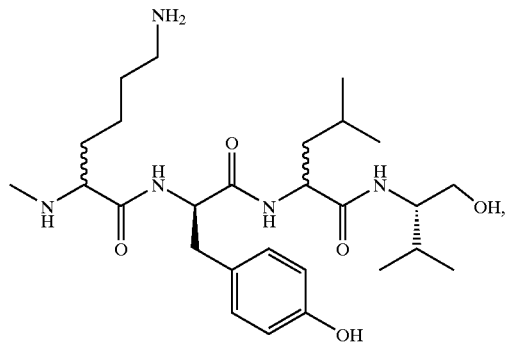

B

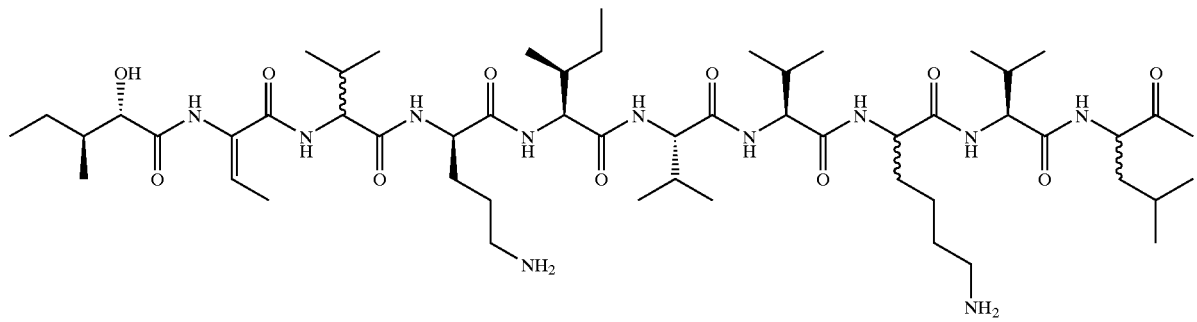

-continued
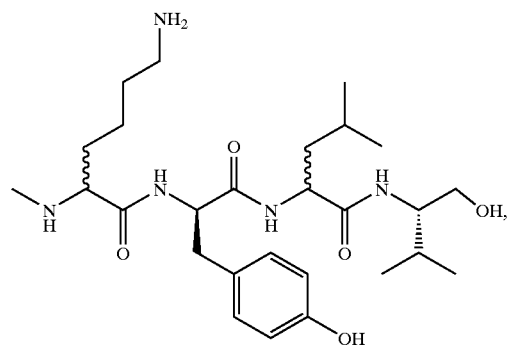
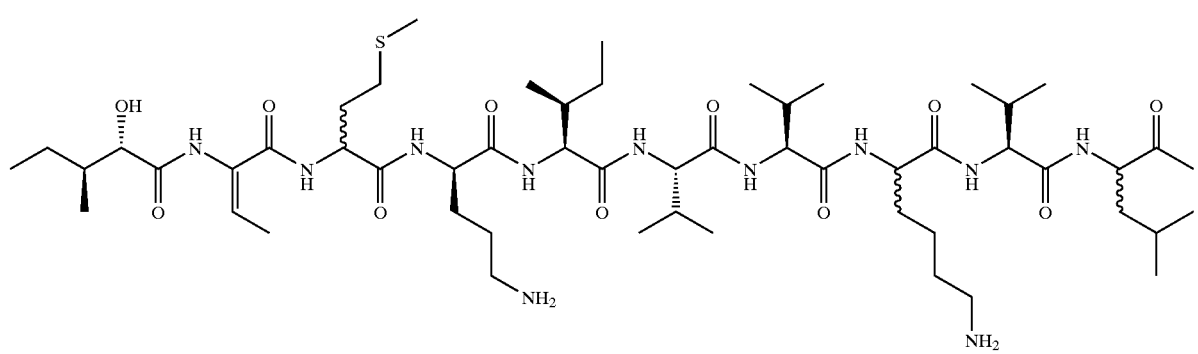
C
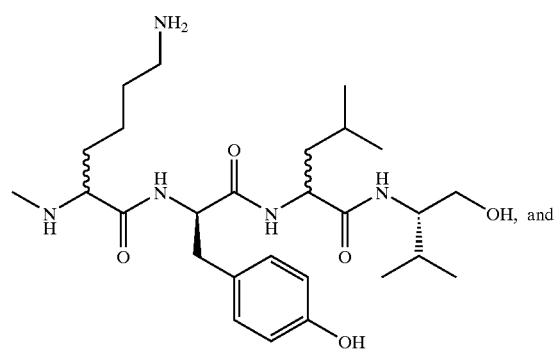
OH, and
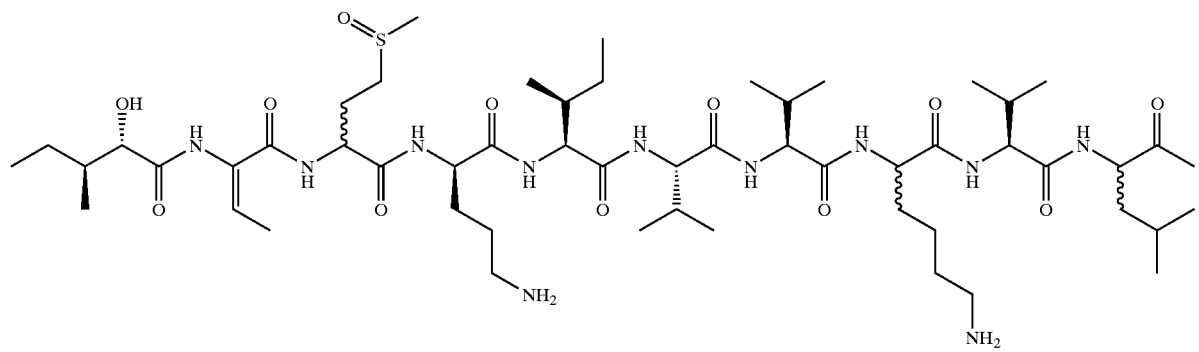
D

-continued

19. The peptide or salt of claim 1, wherein the peptide has the structure:

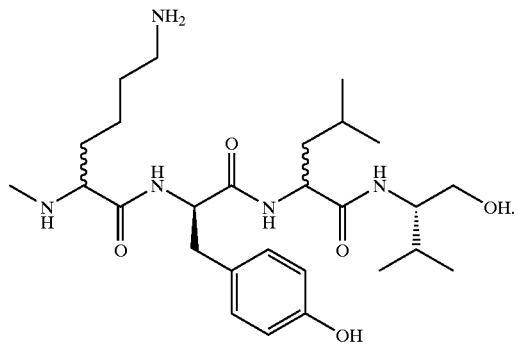

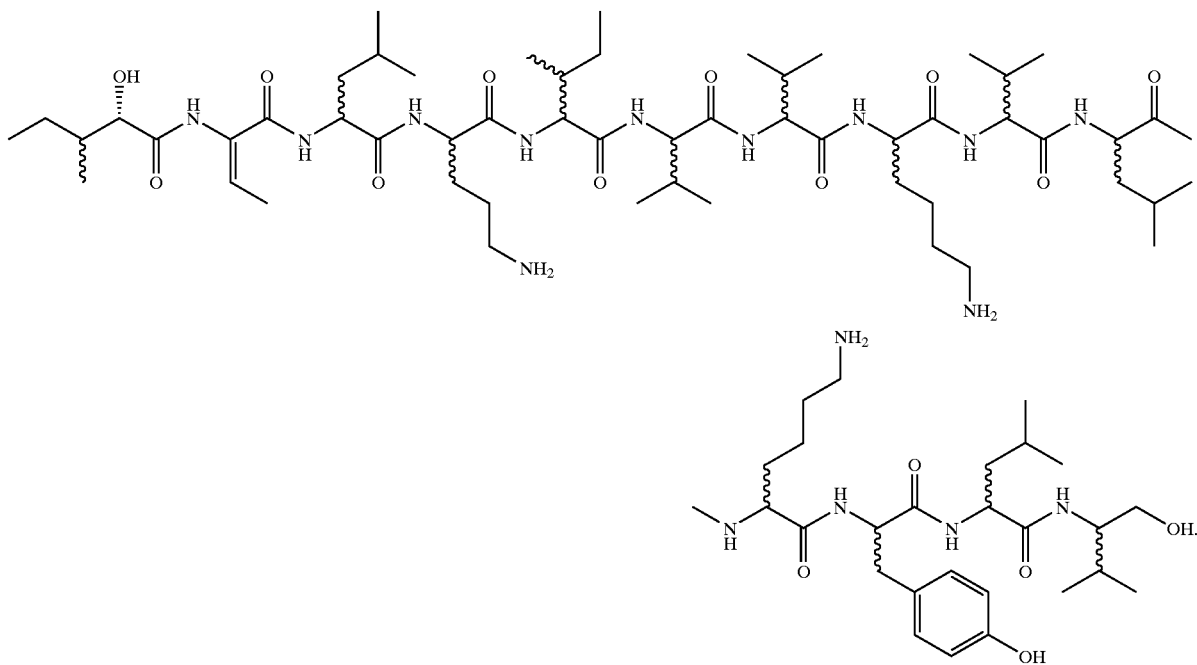

20. A composition comprising a pharmaceutically acceptable carrier and an antibiotic peptide or salt of an antibiotic peptide of formula:

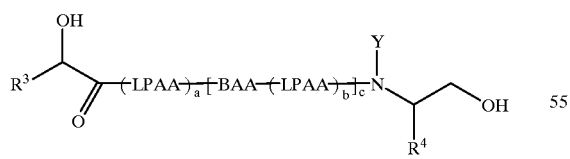

wherein:
a, b, and c are independently selected integers, wherein a=1–5, b=2–6, and c=2–5;
Y is selected from the group consisting of: H; OH; and, a linear, branched or cyclic, saturated or unsaturated alkyl of one to ten carbon atoms;
LPAA is an amino acid residue having the structure —NX—C$^\alpha$R$^1$—CO—, wherein for each LPAA in the peptide, R$^1$ is selected from the group consisting of: hydrogen; a linear, branched or cyclic, saturated or unsaturated alkyl containing one to ten carbons atoms optionally substituted with —OH, —OR, —SH, —SR, —SOCR, —NHCOR, —I, —Br, —Cl, —F, —CN, —O$_2$CR, —CO$_2$R, —CHO, —COR, —CONH$_2$, —CONHR, —CON(R)$_2$, —COSR, —SOR, or —SO$_2$R; benzyl, in which a phenyl ring of the benzyl is optionally substituted with R, —OH, —OR, —O$_2$CR, —SH, —SR, —SOCR —NHCOR, —I, —Br, —Cl, —F, —CN, —CO$_2$R, —CHO, —COR, —CONH$_2$, —CONHR, —CON(R)$_2$, —COSR, —NO$_2$, —SOR, or —SO$_2$R; and, arylalkyl in which an alkyl group of the arylalkyl has two to ten carbon atoms and is linear, branched or cyclic, saturated or unsaturated, optionally substituted with —OH, —OR, —O$_2$CR, —SH, —SR, —SOCR —NHCOR, —I, —Br, —Cl, —F, —CN, —CO$_2$R, —CHO, —COR, —CONH$_2$, —CONHR, —CON(R)$_2$, —COSR, —NO$_2$, —SOR or —SO$_2$R, and in which an aryl ring of the arylalkyl is phenyl, or indole, optionally substituted with R, —OH, —OR, —O$_2$CR, —SH, —SR, —SOCR, —NHCOR, —I, —Br, —Cl, —CN, —CO$_2$R, —CHO, —COR, —CONH$_2$, —CONHR, —CON(R)$_2$, —COSR—NO$_2$, —SOR, or —SO$_2$R;

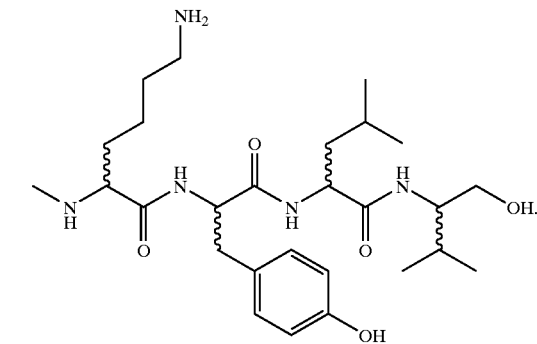

wherein for R¹, R in a substituent is a linear, branched or cyclic, saturated or unsaturated alkyl of one to ten carbon atoms, and providing that when R¹ is joined to C$^\alpha$ by a single bond, H is also present joined to C$^\alpha$; and, for each LPAA in the peptide, X is selected from the group consisting of: H; OH; and, a linear, branched or cyclic, saturated or unsaturated alkyl group containing one to ten carbons;

BAA is an amino acid residue having the structure —NX—CHR$_2$—CO—, wherein for each BAA in the peptide, R² is selected from the group consisting of: a linear, branched or cyclic, saturated or unsaturated alkyl group of one to ten carbons, substituted with one of NH$_2$, NRH, N(R)$_2$, N(R)$_3^+$, —NH—CNH—NH$_2$, or imidazole, and optionally additionally substituted with —OH, —OR, —SH, —SR, —SOCR, —NHCOR, —I, —Br, —Cl, —F, —CN, —CO$_2$R, —CHO, —O$_2$CR, —COR, —CONH$_2$, —CONHR, —CON(R)$_2$, —COSR, —SOR, or SO$_2$R; benzyl in which a phenyl ring of the benzyl is substituted with one of NH$_2$, NRH, N(R)$_2$, or N(R)$_3^+$; and optionally additionally substituted with R, —OH, —OR, —O$_2$CR, —SH, —SR, —SOCR, —NHCOR, —I, —Br, —Cl, —F, —CN, —CO$_2$R, —CHO, —COR, —CONH$_2$, —CONHR, —CON(R)$_2$, —COSR, —NO$_2$, —SOR, or —SO$_2$R; arylalkyl in which an alkyl of the arylalkyl is linear, branched or cyclic, saturated or unsaturated of two to ten carbons, optionally additionally substituted with —OH, —OR, —O$_2$CR, —SH, —SR, —SOCR, —NHCOR, —I, —Br, —Cl, —F, —CN, —CO$_2$R, —CHO, —COR, —CONH$_2$, —CONHR, —CON(R)$_2$, —COSR, —NO$_2$, —SOR, or —SO$_2$, and in which an aryl ring of the arylalkyl is phenyl substituted with one of NH$_2$, NRH, N(R)$_2$, N(R)$_3^+$, indole substituted with one of NH$_2$, NRH, N(R)$_2$, N(R)$_3^+$, pyridine, or imidazole; and wherein the aryl ring is optionally additionally substituted with R, —OH, —OR, —O$_2$CR, —SH, —SR, —SOCR, —NHCOR, —I, —Br, —Cl, —F, —CN, —CO$_2$R, —CHO, —COR, —CONH$_2$, —CONHR, —CON(R)$_2$, —COSR, —NO$_2$, —SOR, or —SO$_2$R; wherein for R², R in a substituent is a linear, branched or cyclic, saturated or unsaturated alkyl of one to ten carbon atoms and for each BAA in the peptide, X is selected from the group consisting of: H; OH; and a linear, branched or cyclic, saturated or unsaturated alkyl of one to ten carbons; and, R³ and R⁴=R¹, and R³ and R⁴ are the same or different.

21. The composition of claim 20, wherein: LPAA is selected from the group consisting of: valine; leucine; isoleucine; tyrosine; phenylalanine; methionine; methionine sulfoxide; threonine; and dehydrobutyrine; BAA is selected from the group consisting of: ornithine; lysine; and arginine; and, R³ and R⁴ are independently selected from the group consisting of: hydrogen; methyl; ethyl; n-propyl; isopropyl; n-butyl; isobutyl; sec-butyl; benzyl; and p-hydroxybenzyl.

22. The composition of claim 21, wherein: a is 1–5; c is 2–5; and, b is 2–6.

23. The composition of claim 21, wherein: a is 2; c is 3; and, b is 2–3.

24. The composition of claim 20, wherein the peptide is selected from the group consisting of structures A, B, C, and D:

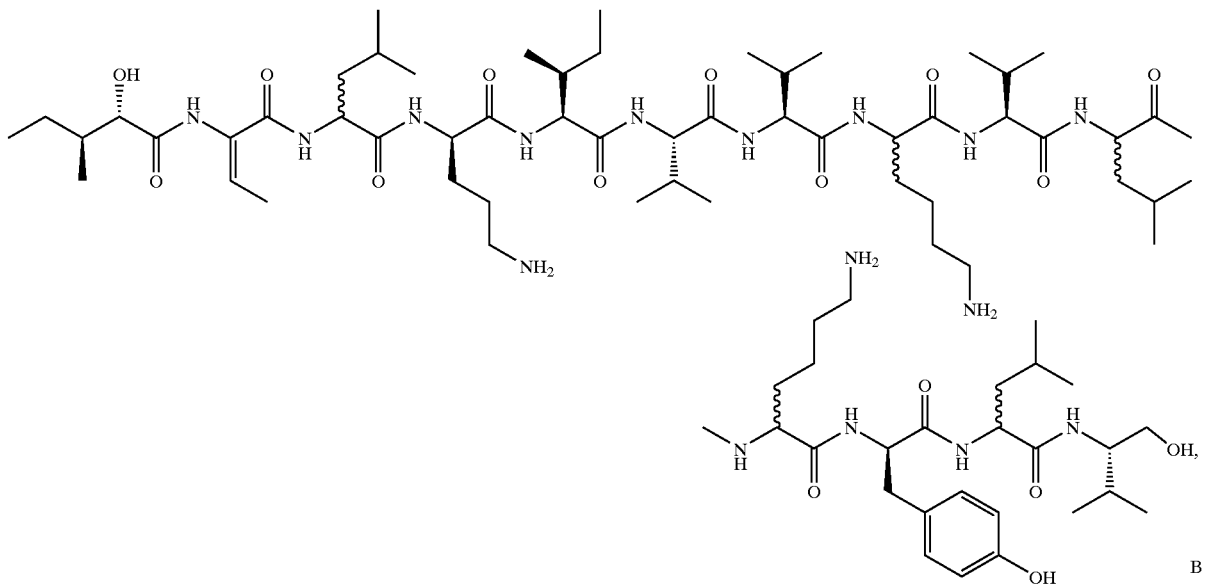

A

B